United States Patent
Daniels

(10) Patent No.: US 9,901,617 B2
(45) Date of Patent: Feb. 27, 2018

(54) CELL PERMEABLE INHIBITORS OF THE SCAFFOLD PROTEIN PLENTY OF SH3 DOMAINS (POSH) OR SH3RFL

(71) Applicant: The Curators of the University of Missouri, Columbia, MO (US)

(72) Inventor: Mark A. Daniels, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/911,939

(22) PCT Filed: Aug. 14, 2014

(86) PCT No.: PCT/US2014/051019
§ 371 (c)(1),
(2) Date: Feb. 12, 2016

(87) PCT Pub. No.: WO2015/023824
PCT Pub. Date: Feb. 19, 2015

(65) Prior Publication Data
US 2016/0193292 A1   Jul. 7, 2016

Related U.S. Application Data

(60) Provisional application No. 61/865,862, filed on Aug. 14, 2013.

(51) Int. Cl.
| | |
|---|---|
| *A61K 38/00* | (2006.01) |
| *C07K 14/47* | (2006.01) |
| *C07K 7/08* | (2006.01) |
| *C12N 7/00* | (2006.01) |
| *A61K 38/17* | (2006.01) |
| *A61K 47/48* | (2006.01) |
| *C07K 14/005* | (2006.01) |

(52) U.S. Cl.
CPC .... *A61K 38/1709* (2013.01); *A61K 47/48246* (2013.01); *C07K 7/08* (2013.01); *C07K 14/005* (2013.01); *C07K 14/47* (2013.01); *C12N 7/00* (2013.01); *A61K 38/00* (2013.01); *C07K 2319/00* (2013.01); *C07K 2319/10* (2013.01); *C12N 2740/16322* (2013.01); *C12N 2740/16371* (2013.01)

(58) Field of Classification Search
CPC ............. A61K 38/00; A61K 38/1709; A61K 47/48246; C07K 14/005; C07K 14/47; C07K 2319/00; C07K 2319/10; C07K 7/08; C12N 2740/16322; C12N 2740/16371; C12N 7/00
USPC ...... 514/19.3, 19.4, 19.6, 21.3, 3.8; 530/324
See application file for complete search history.

(56) References Cited

U.S. PATENT DOCUMENTS

| | | | |
|---|---|---|---|
| 5,595,756 A | * | 1/1997 | Bally .................. A61K 9/1272 264/4.1 |
| 7,250,250 B2 | * | 7/2007 | Alroy ............. C12Y 603/02019 435/4 |
| 2005/0042603 A1 | | 2/2005 | Wang |
| 2007/0128116 A1 | | 6/2007 | Wang et al. |
| 2008/0187538 A1 | | 8/2008 | Alroy et al. |

OTHER PUBLICATIONS

H0YA90 from UniProtKB, pp. 1-6. Integratedinto UniProtKB/TrEMBL on Feb. 22, 2012.*
M7BL61 from UniProtKB, pp. 1-4. Integratedinto UniProtKB/TrEMBL on May 29, 2013.*
I3MMH0 from UniProtKB, pp. 1-5. Integratedinto UniProtKB/TrEMBL on Jul. 11, 2012.*
K0JBK9 from UniProtKB, pp. 1-4. Integratedinto UniProtKB/TrEMBL on Nov. 28, 2012.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Druekes P, "The phosphate recognition site of Escherichia coli maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Neidle, Stephen, ed., Cancer Drug Design and Discovery, Elsevier/Academia Press, 2008, 427-431.*
Gura, T, "Systems for Identifying New Drugs Are Often Faulty," Science, 1997, 1041-1042.*

(Continued)

*Primary Examiner* — Julie Ha
(74) *Attorney, Agent, or Firm* — Shook, Hardy & Bacon, L.L.P.

(57) ABSTRACT

Here, we identify Plenty of SH3 (POSH) and JNK-interacting protein 1 (JIP-1) as a multi-protein scaffold network for TCR-mediated JNK1 activation in CD8+ T-cells. Disruption of the POSH/JIP-1 complex led to profound defects in the activation of JNK1, as well as deficient activation or induction of the transcription factors c-Jun, T-bet and Eomesodermin. Furthermore, disruption of the POSH/JIP complex in CD8+ T-cells resulted in impaired proliferation, decreased cytokine expression and the inability to control tumors. Collectively, these data identify a mechanism for the specific regulation of TCR-dependent JNK1 activation and function that is key for CD8+ T-cell responses. A group of compounds are described that individually or in concert target a common set of biological pathways important in T cell function, activation of innate inflammation, ischemic reperfusion injury, HIV release and oncogenesis.

10 Claims, 66 Drawing Sheets

(56) References Cited

OTHER PUBLICATIONS

Auberbach et al., "Angiogenesis assays: Problems and pitfalls," Cancer and Metastasis Reviews, 2000, 19: 167-172.*
Jain RK, "Barriers to Drug Delivery in Solid Tumors," Scientific American, 1994, 58-65.*
Sporn et al., "Chemoprevention of cancer," Carcinogenesis, 2000, 21(3): 525-530.*
International Search Report with Written Opinion dated Feb. 4, 2015 in Application No. PCT/US2014/51019, 18 pages.
Lyons et al. Regulation of the Pro-apoptotic Scaffolding Protein POSH by Akt. J Biol Chem. 2007, vol. 282(30), p. 21987-97.
Rahmat et al. Synergistic effects of conjugating cell penetrating peptides and thiomers on non-viral transfection efficiency. Biomaterials. 2012, vol. 33(7), p. 2321-6.
Shen et al. Modulation of nuclear internalization of Tat peptides by fluorescent dyes and receptor-avid peptides. FEBS Lett. 2007, vol. 581(9), p. 1793-1799.
Cunningham et al. The POSH/JIP-1 scaffold network regulates TCR-mediated JNK1 signals and effector function in CD8(+) T cells. Eur J Immunol. Dec. 2013, vol. 43(12), p. 3361-71. Epub Sep. 10, 2013.
International Preliminary Report on Patentability dated Feb. 25, 2016 in Application No. PCT/US2014/051019, 11 pages.

* cited by examiner

```
Grkkrrqrrr-pp- egkepgdlkfskgdiiilrr    Tat-POSH SH3.1  (SEQ ID NO: 10)
Grkkrrqrrr-pp- keadkdclpfakddvltvir    Tat-POSH SH3.2  (SEQ ID NO: 11)
Grkkrrqrrr-pp- rkedelelrkgemflvfer     Tat-POSH SH3.3  (SEQ ID NO: 12)
Grkkrrqrrr-pp- pqseaelelkegdivfvhkk    Tat-POSH SH3.4  (SEQ ID NO: 13)
```

*FIG. 3B.*

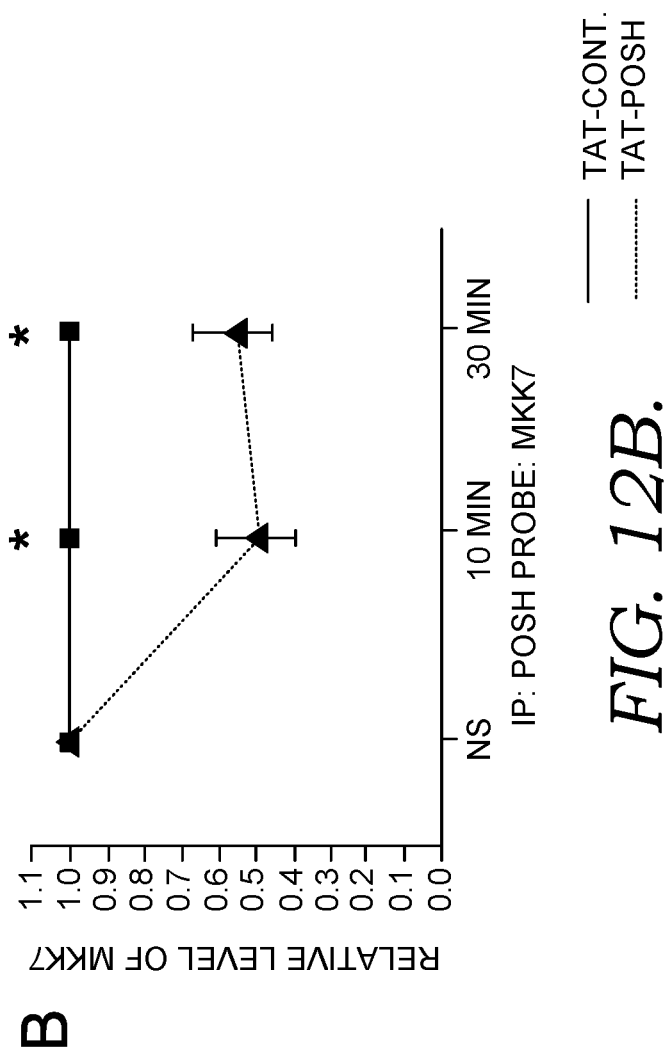

SEQUENCE LISTING

```
<160> NUMBER OF SEQ ID NOS: 16

<210> SEQ ID NO 1
<211> LENGTH: 20
<212> TYPE: PRT
<213> ORGANISM: Homo sapiens

<400> SEQUENCE: 1

Glu Gly Lys Glu Pro Gly Asp Leu Lys Phe Ser Lys Gly Asp Ile Ile
1               5                   10                  15

Ile Leu Arg Arg
            20

<210> SEQ ID NO 2
<211> LENGTH: 20
<212> TYPE: PRT
<213> ORGANISM: Homo sapiens

<400> SEQUENCE: 2

Lys Glu Ala Asp Lys Asp Cys Leu Pro Phe Ala Lys Asp Asp Val Leu
1               5                   10                  15

Thr Val Ile Arg
            20

<210> SEQ ID NO 3
<211> LENGTH: 19
<212> TYPE: PRT
<213> ORGANISM: Homo sapiens

<400> SEQUENCE: 3

Arg Lys Glu Asp Glu Leu Glu Leu Arg Lys Gly Glu Met Phe Leu Val
1               5                   10                  15

Phe Glu Arg

<210> SEQ ID NO 4
<211> LENGTH: 20
<212> TYPE: PRT
<213> ORGANISM: Homo sapiens

<400> SEQUENCE: 4

Pro Gln Ser Glu Ala Glu Leu Glu Leu Lys Glu Gly Asp Ile Val Phe
1               5                   10                  15

Val His Lys Lys
            20

<210> SEQ ID NO 5
<211> LENGTH: 10
<212> TYPE: PRT
```

<213> ORGANISM: Human immunodeficiency virus

<400> SEQUENCE: 5

Gly Arg Lys Lys Arg Arg Gln Arg Arg Arg
1               5                   10

<210> SEQ ID NO 6
<211> LENGTH: 60
<212> TYPE: PRT
<213> ORGANISM: Homo sapiens

<400> SEQUENCE: 6

Pro Gln Leu Pro Cys Ala Lys Ala Leu Tyr Asn Tyr Glu Gly Lys Glu
1               5                   10                  15

Pro Gly Asp Leu Lys Phe Ser Lys Gly Asp Ile Ile Ile Leu Arg Arg
                20                  25                  30

Gln Val Asp Glu Asn Trp Tyr His Gly Glu Val Asn Gly Ile His Gly
            35                  40                  45

Phe Phe Pro Thr Asn Phe Val Gln Ile Ile Lys Pro
        50                  55                  60

<210> SEQ ID NO 7
<211> LENGTH: 53
<212> TYPE: PRT
<213> ORGANISM: Homo sapiens

<400> SEQUENCE: 7

Lys Ala Leu Tyr Asp Phe Glu Val Lys Asp Lys Glu Ala Asp Lys Asp
1               5                   10                  15

Cys Leu Pro Phe Ala Lys Asp Asp Val Leu Thr Val Ile Arg Arg Val
                20                  25                  30

Asp Glu Asn Trp Ala Glu Gly Met Leu Ala Asp Lys Ile Gly Ile Phe
            35                  40                  45

Pro Ile Ser Tyr Val
        50

<210> SEQ ID NO 8
<211> LENGTH: 62
<212> TYPE: PRT
<213> ORGANISM: Homo sapiens

<400> SEQUENCE: 8

Thr Arg Pro Ser Val Tyr Val Ala Ile Tyr Pro Tyr Thr Pro Arg Lys
1               5                   10                  15

Glu Asp Glu Leu Glu Leu Arg Lys Gly Glu Met Phe Leu Val Phe Glu
                20                  25                  30

Arg Cys Gln Asp Gly Trp Phe Lys Gly Thr Ser Met His Thr Ser Lys
            35                  40                  45

Ile Gly Val Phe Pro Gly Asn Tyr Val Ala Pro Val Thr Arg
        50                  55                  60

<210> SEQ ID NO 9
<211> LENGTH: 54
<212> TYPE: PRT
<213> ORGANISM: Homo sapiens

<400> SEQUENCE: 9

His Arg Val Val Val Ser Tyr Pro Pro Gln Ser Glu Ala Glu Leu Glu
1               5                   10                  15

Leu Lys Glu Gly Asp Ile Val Phe Val His Lys Lys Arg Glu Asp Gly

-continued

```
                 20                  25                  30

Trp Phe Lys Gly Thr Leu Gln Arg Asn Gly Lys Thr Gly Leu Phe Pro
         35                  40                  45

Gly Ser Phe Val Glu Asn
     50

<210> SEQ ID NO 10
<211> LENGTH: 32
<212> TYPE: PRT
<213> ORGANISM: Artificial
<220> FEATURE:
<223> OTHER INFORMATION: Chimeric peptide

<400> SEQUENCE: 10

Gly Arg Lys Lys Arg Arg Gln Arg Arg Pro Pro Glu Gly Lys Glu
1               5                   10                  15

Pro Gly Asp Leu Lys Phe Ser Lys Gly Asp Ile Ile Leu Arg Arg
            20                  25                  30

<210> SEQ ID NO 11
<211> LENGTH: 32
<212> TYPE: PRT
<213> ORGANISM: Artificial
<220> FEATURE:
<223> OTHER INFORMATION: Chimeric peptide

<400> SEQUENCE: 11

Gly Arg Lys Lys Arg Arg Gln Arg Arg Pro Pro Lys Glu Ala Asp
1               5                   10                  15

Lys Asp Cys Leu Pro Phe Ala Lys Asp Asp Val Leu Thr Val Ile Arg
            20                  25                  30

<210> SEQ ID NO 12
<211> LENGTH: 31
<212> TYPE: PRT
<213> ORGANISM: Artificial
<220> FEATURE:
<223> OTHER INFORMATION: Chimeric peptide

<400> SEQUENCE: 12

Gly Arg Lys Lys Arg Arg Gln Arg Arg Pro Pro Arg Lys Glu Asp
1               5                   10                  15

Glu Leu Glu Leu Arg Lys Gly Glu Met Phe Leu Val Phe Glu Arg
            20                  25                  30

<210> SEQ ID NO 13
<211> LENGTH: 32
<212> TYPE: PRT
<213> ORGANISM: Artificial
<220> FEATURE:
<223> OTHER INFORMATION: Chimeric peptide

<400> SEQUENCE: 13

Gly Arg Lys Lys Arg Arg Gln Arg Arg Pro Pro Pro Gln Ser Glu
1               5                   10                  15

Ala Glu Leu Glu Leu Lys Glu Gly Asp Ile Val Phe Val His Lys Lys
            20                  25                  30

<210> SEQ ID NO 14
<211> LENGTH: 20
<212> TYPE: PRT
<213> ORGANISM: Mus musculus

<400> SEQUENCE: 14
```

```
Asn Ala Tyr Asp Lys Thr Ala Leu Ala Leu Lys Glu Gly Glu Leu Val
1               5                   10                  15

Lys Val Thr Lys
            20

<210> SEQ ID NO 15
<211> LENGTH: 20
<212> TYPE: PRT
<213> ORGANISM: Mus musculus

<400> SEQUENCE: 15

Pro Arg Lys Glu Asp Glu Leu Glu Leu Arg Lys Gly Glu Met Phe Leu
1               5                   10                  15

Val Phe Glu Arg
            20

<210> SEQ ID NO 16
<211> LENGTH: 20
<212> TYPE: PRT
<213> ORGANISM: Mus musculus

<400> SEQUENCE: 16

Arg Pro Lys Arg Pro Thr Thr Leu Asn Leu Phe Pro Gln Val Pro Arg
1               5                   10                  15

Ser Gln Asp Thr
            20
```

CELL PERMEABLE INHIBITORS OF THE SCAFFOLD PROTEIN PLENTY OF SH3 DOMAINS (POSH) OR SH3RFL

FIELD OF THE INVENTION

The present invention relates to a group of compounds that individually or in concert target a common set of biological pathways important in T cell function, activation of innate inflammation, ischemic reperfusion injury, HIV release and oncogenesis.

SEQUENCE LISTING

A text file in compliance with ASCII and having a ".txt" extension has been electronically submitted via EFS-Web. The text file named "Sequence Listing" was created on Aug. 13, 2014, and is 1.4 KB. The text file is expressly incorporated by reference herein in its entirety.

BACKGROUND

Upon infection, T-cell activation and differentiation are initiated through TCR engagement of peptide-MHC molecules on the surface of APCs in the context of co-stimulation and inflammatory cytokines. These cues trigger numerous signal transduction cascades, whose integration is 'translated' into changes in gene transcription, protein activity and expression. This ultimately leads to the development of effector function and T-cell-mediated immunity. The MAPK SAPK/JNK cascade plays a major role in regulating a variety of fate decisions including activation, proliferation, differentiation and death. Three genes encode the JNK family members. JNK1 and JNK2 are ubiquitously expressed, whereas the expression of JNK3 is restricted to the brain, heart and testis. Whilst each JNK isoform is ascribed a unique function, how activation of each is independently regulated is not well understood.

Activation of JNK is important for shaping both the innate and adaptive immune response. For innate immune responses, the inflammatory cytokines TNF and IL-1 induce JNK activity. JNK2 and IKKβ induce the production of pro-inflammatory cytokine response to viral dsRNA. Inflammation dependent activation of PLCγ, JNK and NF-κB enhances the ability of dendritic cells and epithelium tissue to induce Th17 responses. JNK signaling is implicated in regulating pro-inflammatory cytokine production, joint inflammation and destruction in rheumatoid arthritis. JNK is also required for polarization of pro-inflammatory macrophages, obesity-induced insulin resistance and inflammation in adipose tissue.

For T lymphocytes, JNK activation plays different roles depending on the T-cell type, the maturation state and the milieu of the responding cell. For example, in developing thymocytes JNK activation appears to have a role in negative selection and the induction of apoptosis, while in mature T cells it regulates the development of effector functions. In mature $CD4^+$ T cells JNKs inhibit Th2 differentiation by suppressing NFAT/JunB signaling and drive Th1 by inducing IL-12Rβ2 expression. Regulation of Treg function through the glucocorticoid-induced tumor necrosis receptor (GITR) also depends on JNK signaling. In addition, JNK1 and JNK2 have distinct functions even within the same type of T cell. For $CD8^+$ T cells, JNK1 functions downstream of the TCR to induce CD25, enabling a proliferative response to IL-2 (FIG. 1). $JNK1^{-/-}$ $CD8^+$ T cells demonstrate enhanced apoptosis in an in vivo anti-viral immune response. By contrast, cells lacking JNK2 are hyper-proliferative due to increased production of IL-2. Furthermore, JNK1 and JNK2 have divergent effects on effector function. JNK1 promotes IFN-γ and Perforin production and optimal killing of tumor cells. Conversely, $JNK2^{-/-}$ $CD8^+$ T cells express more IFN-γ and Granzyme B and exhibit enhanced tumor clearance. Together, these findings illustrate the extreme importance of JNK in an immune response and demonstrate the need to understand the specific regulation of JNK1 and JNK2 to control the outcome of these responses.

The mechanisms that regulate the independent activation of the individual JNK isoforms are poorly understood. The functional specificity of a number of MAPK signaling pathways has been attributed to their regulation by scaffold molecules. Scaffolds provide means for both spatial regulation and network formation that increase the number of outcomes possible when activating a given pathway. Numerous scaffold proteins have been identified for the JNK signaling pathway including β-arrestin-2, CrkII, JIP-1, plenty of SH3s (POSH), and Carma1/Bcl10. Interestingly, Carma1/Bcl10 selectively regulates JNK2 activation in $CD8^+$ T cells. However, the scaffold proteins specific for TCR-mediated JNK1 activation is less clear.

The TCR connects to JNK activation through the guanine exchange factor (GEF) Vav1 and the adaptor/GEF complex, Grb2/SOS. These molecules are recruited to phosphorylated tyrosine residues on the linker for activation of T cells (LAT). Importantly, both Vav1 and Grb2/SOS activate Rac1 and deficiencies in either lead to significant reduction in JNK signaling. POSH (Plenty of SH3) was initially identified as a scaffold protein that linked active Rac1 to JNK and NF-κB activation, while JIP-1 is a scaffold that facilitates JNK activation through the recruitment of MLK and MKK7. Interestingly, in neurons the association of POSH and JIP-1 mediates JNK activation and apoptosis. However, the role of POSH and JIP-1 in TCR-dependent JNK activation is not known.

POSH is a ubiquitously expressed scaffold molecule that assembles components of signaling pathways that lead to regulation of a number of essential cellular functions. Many of the functions are specific to the type of tissue or the maturation state of the cell. Inhibitors are designed to interfere with the assembly of signaling module and block signals.

Here we investigated the role of POSH in JNK activation in $CD8^+$ T cells. Using a peptide inhibitor strategy, we determined that the interaction between POSH and JIP-1 is required for JNK1, but not JNK2, phosphorylation and T-cell effector function. Most interestingly, the disruption of the POSH/JIP-1 complex results in functional defects that pheno-copy $JNK1^{-/-}$ T cells. Un-coupling POSH and JIP-1 resulted in decreased proliferation, defects in IFN-γ and TNF-α expression and markedly reduced tumor clearance. Correspondingly, the POSH/JIP-1 regulation of JNK1 was also important for the induction of the transcription factors c-Jun, T-bet and Eomesodermin (Eomes), which play important roles in programming effector function. Collectively, these data indicate for the first time, that POSH and the POSH/JIP-1 scaffold network is specifically required for JNK1 dependent T-cell differentiation and effector function in mature $CD8^+$ T cells.

SUMMARY

In one embodiment of the invention, a group of compounds that individually or in concert target a common set of biological pathways important in T cell function, activation of innate inflammation, ischemic reperfusion injury, HIV release and oncogenesis. This group of compounds comprises a polypeptide with a sequence EGKEPGDLKF-SKGDIIILRR (SEQ ID NO: 1) or KEADKDCLPFAKD-DVLTVIR (SEQ ID NO: 2) or RKEDELELRKGEM-FLVFER (SEQ ID NO: 3) or PQSEAELELKEGDIVFVHKK (SEQ ID NO: 4).

Other embodiments provide a method to use peptide inhibitor strategy to uncouple POSH and JIP-1 resulting in the disruption of the POSH/JIP-1 complex which causes functional defects that phenocopy JNK1$^{-/-}$ T cells. This uncoupling of POSH and JIP-1 in the POSH/JIP-1 complex resulted in decreased proliferation, defects in IFN-γ and TNF-α expression and markedly reduced tumor clearance.

Embodiments of the present invention provide methods and constructs for inhibiting and disrupting the POSH/JIP-1 network which leads to defective tumor clearance in vivo and transiently inhibits T-bet and blocks Eomes activation, which play important roles in programming effector function. Collectively, the embodiments of the present invention identify a method and a group of compounds for specific regulation of TCR-dependent JNK1 activation and function that is key for CD8$^+$ T-cell responses.

BRIEF DESCRIPTION OF THE DRAWING

The patent or application file contains at least one drawing executed in color. Copies of this patent or patent application publication with color drawing(s) will be provided by the Office upon request and payment of the necessary fee.

Embodiments are described in detail below with reference to the attached drawing figures and pictures, wherein:

FIGS. 3(A) to 3(B) demonstrate the different sequences of Tat-POSH compounds, with FIG. 3(A) depicting SEQ ID NO: 6, SEQ ID NO: 7, SEQ ID NO: 8, and SEQ ID NO: 9, and FIG. 3(B) depicting SEQ ID NO: 10, SEQ ID NO: 11, SEQ ID NO: 12, and SEQ ID NO: 13.

FIGS. 12(A) to 12(E) demonstrate the determination of the configuration of the POSH/JIP-1 scaffold complex

DETAILED DESCRIPTION

The small peptides of SEQ ID NO: 1 to SEQ ID NO: 4 are a group of compounds that individually or in concert target a common set of biological pathways important in T cell function, activation of innate inflammation, ischemic reperfusion injury, HIV release and oncogenesis. The targeted pathways converge on (or are regulated by) POSH, a specific scaffold molecule, that functions to assemble components of signaling pathways that regulate basic cell biological processes of division, survival, death, development and differentiation. The deregulation of these pathways is implicated in cancer, autoimmunity, inflammation, as well as the function and development of T cells and neurons. These compounds manipulate biological processes for the following disease treatments:

Auto immunity: treatment to reduce deleterious effects of the activation of targeted immune cells;

Ischemic reperfusion injury: prevent neuronal apoptosis associated with ischemic reperfusion;

Anti-tumor: to induce death or to inhibit growth and metastases in a various tumor types; and HIV: reduce or prevent viral assembly and release of HIV-1.

These compounds (SEQ ID NO: 1 to SEQ ID NO: 4) provide a significant advantage over currently available methodologies in that they are effective when used individually or in combinations that target multiple points of the same pathway. This provides the increased efficacy and minimizes potential issues of resistance. Furthermore these compounds can easily manufactured and targeted to specific cells or tissue to minimize unwanted side effects.

The efficacy of Tat-POSH.SH3.3 (SEQ ID NO: 12) has been tested in a number of cells. It is able to significantly reduce the effector function of CD8 T cells in vitro and in vivo It has been used to effectively manipulate the viability of tumor cells. It can kill leukemia cell lines (human and mouse) and stop proliferation of other leukemia cell lines that developed from a different ontological stage. It has a modest but significant effect on the survival of one human breast cancer clinical isolate. It kills a TPL-2 dependent lung cancer cell line. It reduces viral production by 40-50% in HIV infected cells in vitro. Additional testing has been done on Tat-POSH SH3.1, -.2, -.4 (SEQ ID NO: 10, SEQ ID NO: 11, and SEQ ID NO: 13, respectively).

Figure 1:
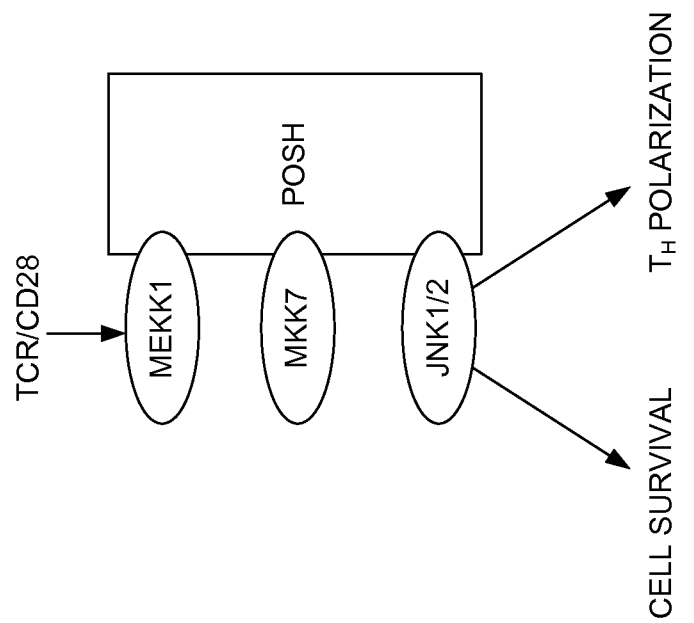
FIG. 1 a schematic illustrates how TCR/CD28 regulates cell survival and T$_H$ polarization through POSH scaffold.
Figure 2:
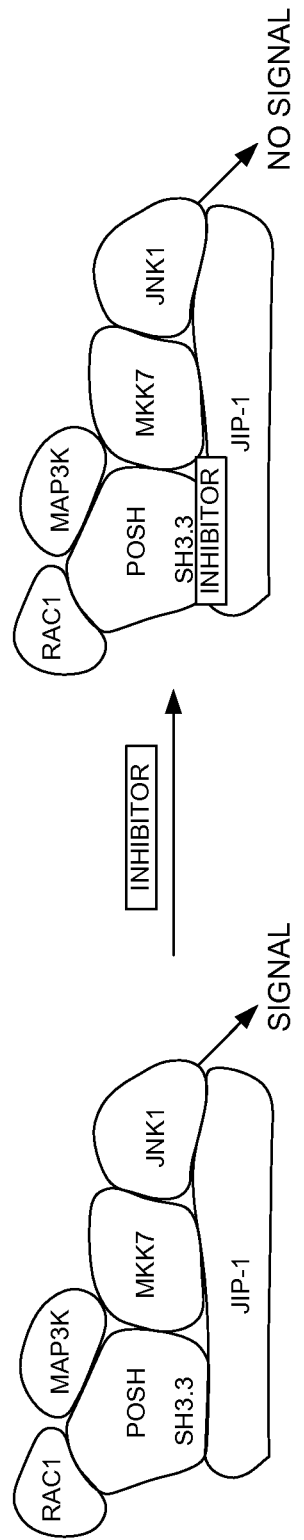
FIG. 2 illustrates how POSH SH3.3 inhibitor leads to the loss of JNK1 signal.

The target is a critical component of a scaffold network that can be targeted from a number of unique points of regulation, either individually or in combination, to both increase efficacies of treatment and to minimize resistance or escape variants. FIG. 2 shows how Tat-POSH SH3.3 (SEQ ID NO: 12) can inhibit the binding between POSH and JIP-1 resulting in the disruption of POSH/JIP1 complex resulting in loss of JNK1 signaling and cause functional defects that phenocopy JNK$^{-/-}$ T cells. In tests performed in leukemic and normal thymocytes, the product effectively kills leukemic cells where normal cells are not affected, suggesting a potential of minimizing risk of treatment side effects. Interestingly the targeted sequences are highly conserved from human back through the *Xenopus* which makes testing the potential function, efficacy and side effects less costly.

Figure 3A:
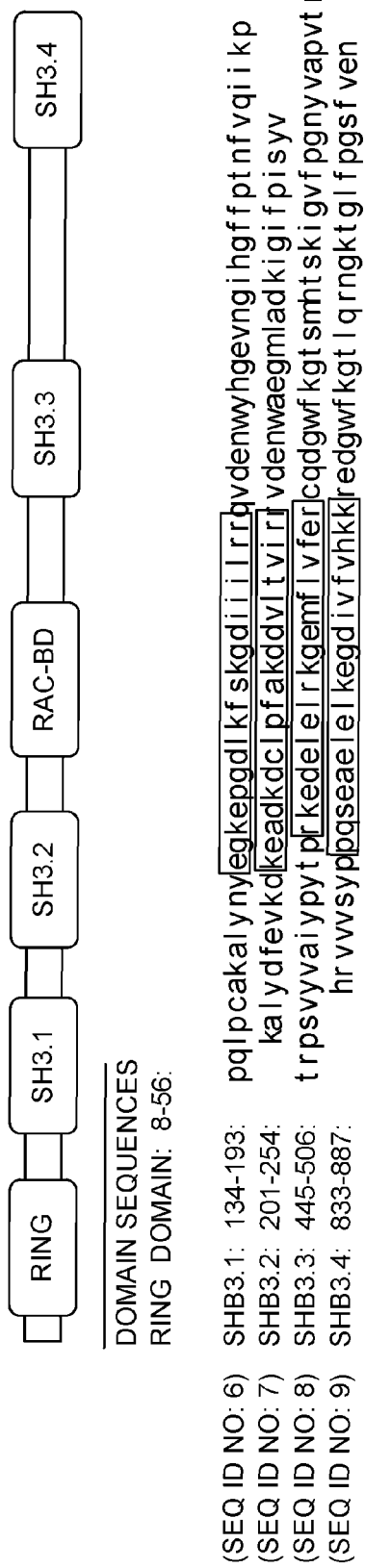
Figure 4:
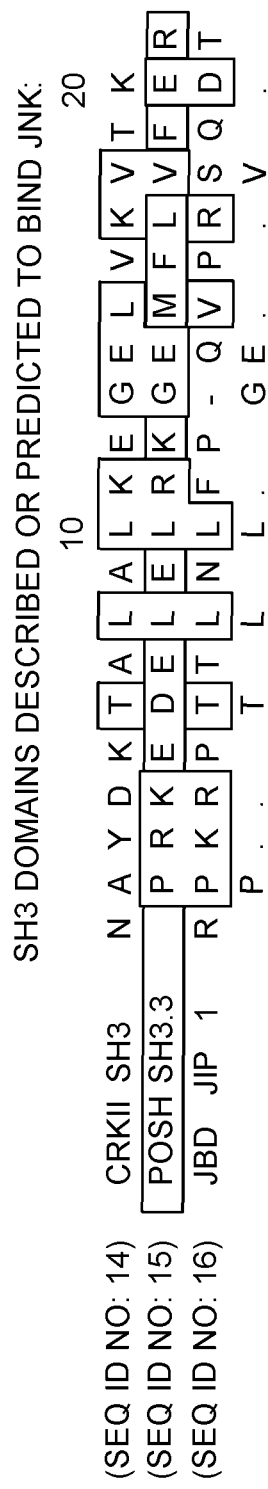
FIG. 4 demonstrates a schematic of design logic for Tat-POSH SH3.3, depicting SEQ ID NO: 14, SEQ ID NO: 15, and SEQ ID NO: 16.

Using algorithms for sequence prediction, sequences (FIG. 3A, boxed sequences SEQ ID NO: 1-SEQ ID NO: 4) were chosen for their predicted or tested binding function and synthesized to contain the protein-transduction domain of HIV-Tat (of sequence GRKKRRQRRR (SEQ ID NO: 5), FIG. 3B) plus pp linker via standard peptide synthesis methodology. These sequences can be modified to increase efficacy/specificity for desired target and could potentially include additional residues within the SH3 domains shown in FIG. 3A. Schematic for design logic for Tat-POSH SH3.3 (SEQ ID NO: 12) and SH3 domains described or predicted to bind JNK are shown in FIG. 4 (SEQ ID NO: 14-SEQ ID NO: 16).

It will be appreciated that there may be a number of per mutational possibilities of the polypeptides; the size and sequence of the polypeptide of SEQ ID NO: 1-SEQ ID NO: 4. In any case, the ability of the polypeptides of SEQ ID NO: 1-SEQ ID NO: 4 to bind POSH (Plenty of SH3 Domains) and inhibit POSH scaffold networks may be tested by one of ordinary skill using the methods described in the examples below.

As indicated above, the described polypeptides are useful for prevention and treatment of (relieving or improving) a condition in a patient, including, without limitation: cancer, inflammation and infection. The polypeptides may be linked to any variety of cell penetrating peptides (CPPs) known in the art.

The POSH/JIP-1 Scaffold Network Regulates JNK1 Activation.

Figure 5A:
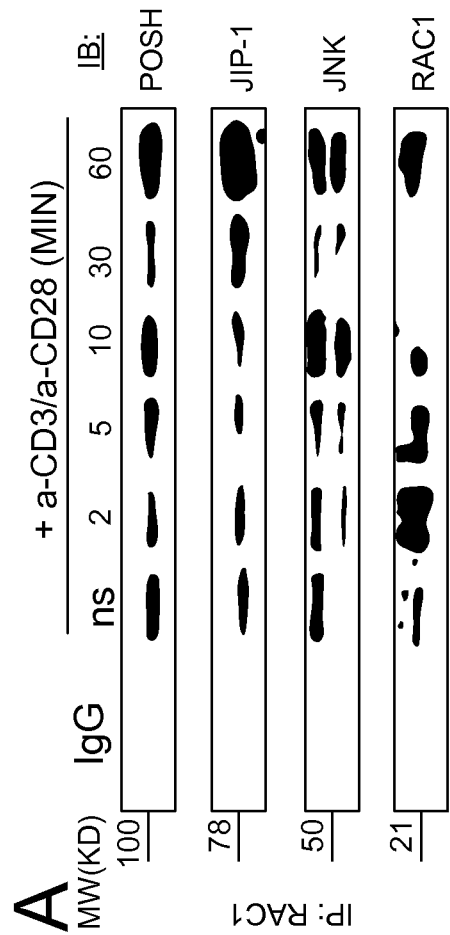
FIGS. 5(A) to 5(E) illustrate the binding of the scaffold protein POSH to JIP-1 and JNK in CD8$^+$ T cells.
Figure 5B:
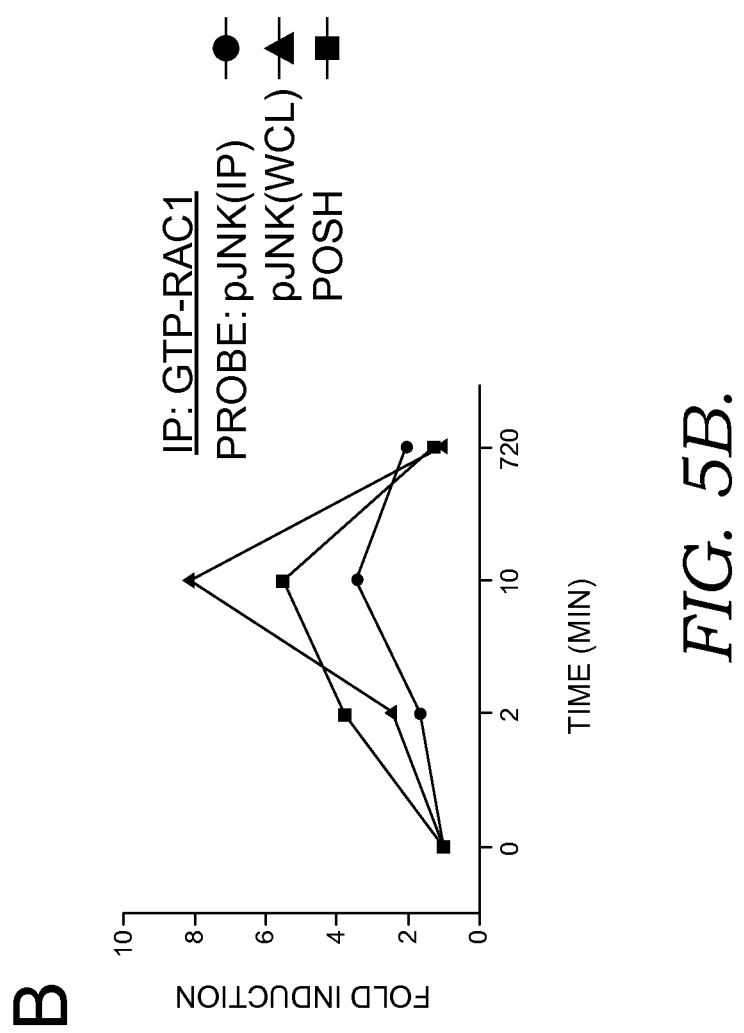

POSH is a Rac1 dependent scaffold of JNK signaling. To identify a role for POSH in TCR-mediated JNK activation, we established its ability to bind components of the JNK signaling cascade in CD8+ T cells. For this, OT-1 TCR transgenic blasts (CTL) were re-stimulated with OVA-Tetramer (Tet)/α-CD28 and subjected to IP with antibodies against Rac1. Co-immunoprecipitation (Co-IP) of components of the JNK signaling pathway was assessed by immunoblot. POSH, JIP-1, JNK and MKK7 were all found in complex with Rac1 (FIG. 5A, data not shown). Interestingly, pull downs of GTP bound (active) Rac1 indicated that the association POSH and JNK increased with JNK activation (FIG. 5B). Given the importance of JNK in regulating T-cell differentiation, we also wished to assess the association of these molecules in naïve cells. However, naïve cells have low expression of POSH, JIP-1 and JNK which greatly reduces the ability to detect their association by classic IP. To circumvent this problem we performed Co-IP analyses by flow cytometry (IP-FCM) using α-Rac1, α-POSH and α-JIP-1 antibodies covalently linked to latex beads. The beads were incubated with the lysates washed and probed with antibodies against the Co-IP target. The levels of associated molecules (secondary analyte/Co-IP target) were quantified relative to IP target (primary analyte/loading control). Specificity was determined by comparison to both isotype and negative control antibodies (FIG. 5 and FIG. 6). This remarkable methodology allowed us to measure native molecular interactions in primary T cells with low analyte concentrations, very small input sample size and high sensitivity. For IP-FCM quantification controls and Tat-POSH inhibitor specificity controls, OT-I T cells were stimulated with OVA-Tet for 24 hours. Cells were then lysed and subjected to IP-FCM using α-Rac-1, α-POSH or α-JIP-1 beads (FIG. 6A). Shaded histogram represents the staining of an isotype control. The black line histogram represents the staining of ERK1/2 to represent a negative control, as ERK is not expected to be in the POSH/JIP-1 complex. These two negative controls were used to establish significance of shift above background. To control for specificity of the Tat-POSH inhibitor we examined the activity of phospho CD3 zeta, ZAP70, LAT (representative blot shown). In FIG. 6B, graphs depict fold induction normalized to non-stimulated. Numbers were quantified against total protein and beta actin loading control. Errors are ±SD, n=6. ERK and p-38 in T cells stimulated with OVA-Tet/αCD28 by immunoblot (FIG. 6C-D, see also controls for NF-KB activation, FIG. 8D and apoptosis, FIG. 13D). All data in FIG. 6A, C-D are representative of n≥3 independent experiments.

Figure 5C:
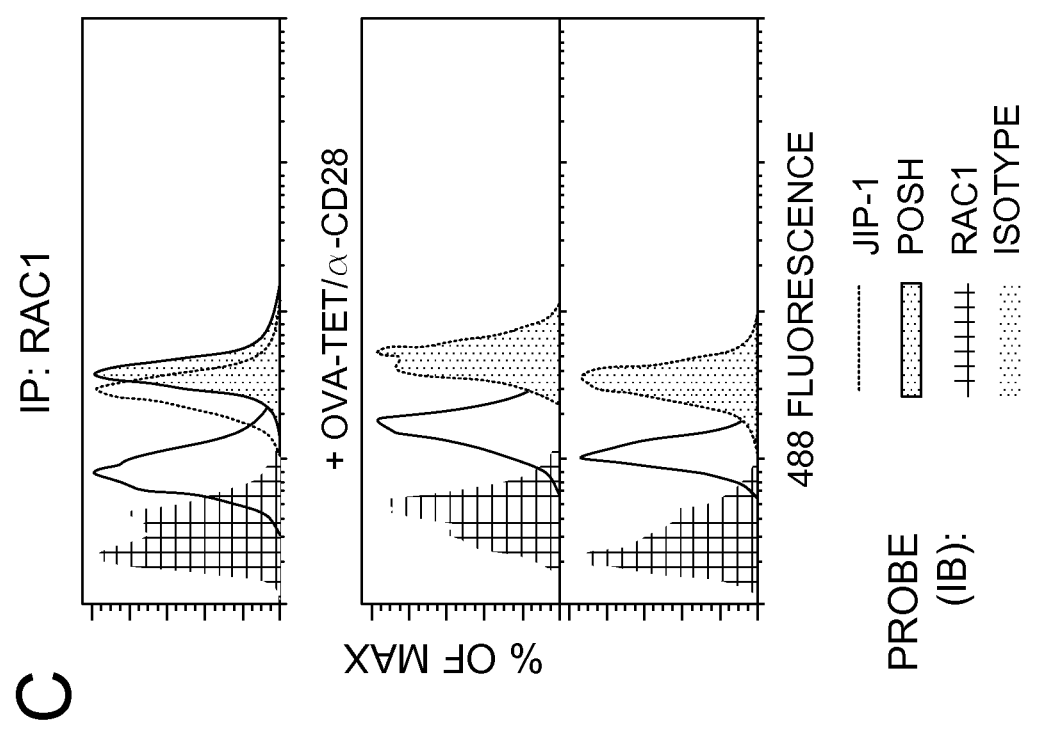
Figure 5D:
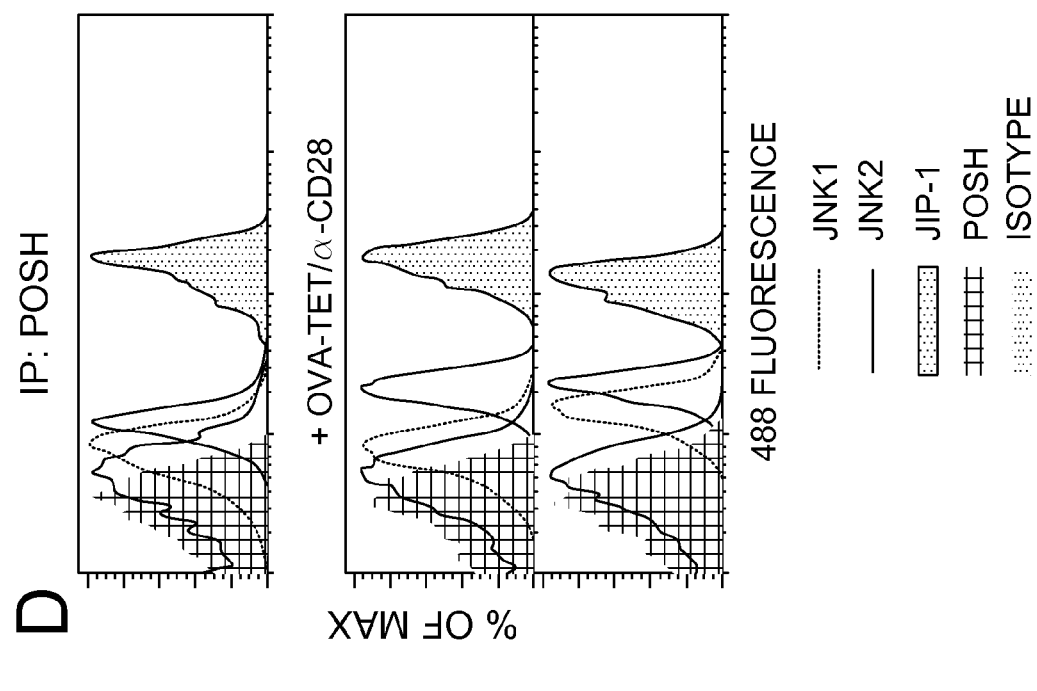
Figure 5E:
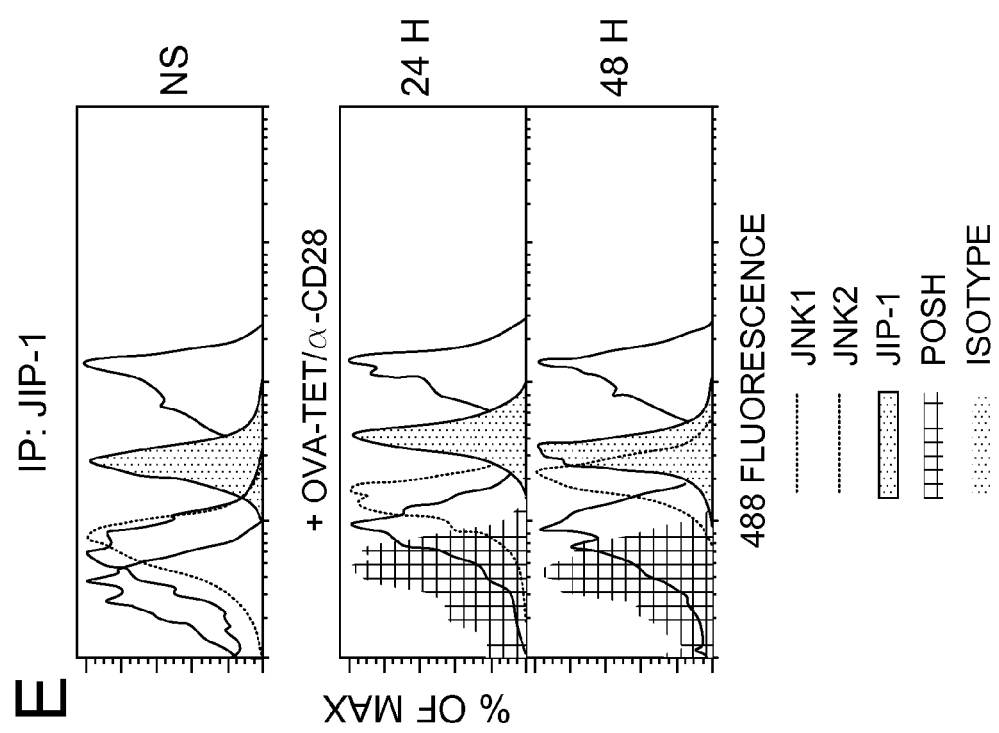
Figure 6A:
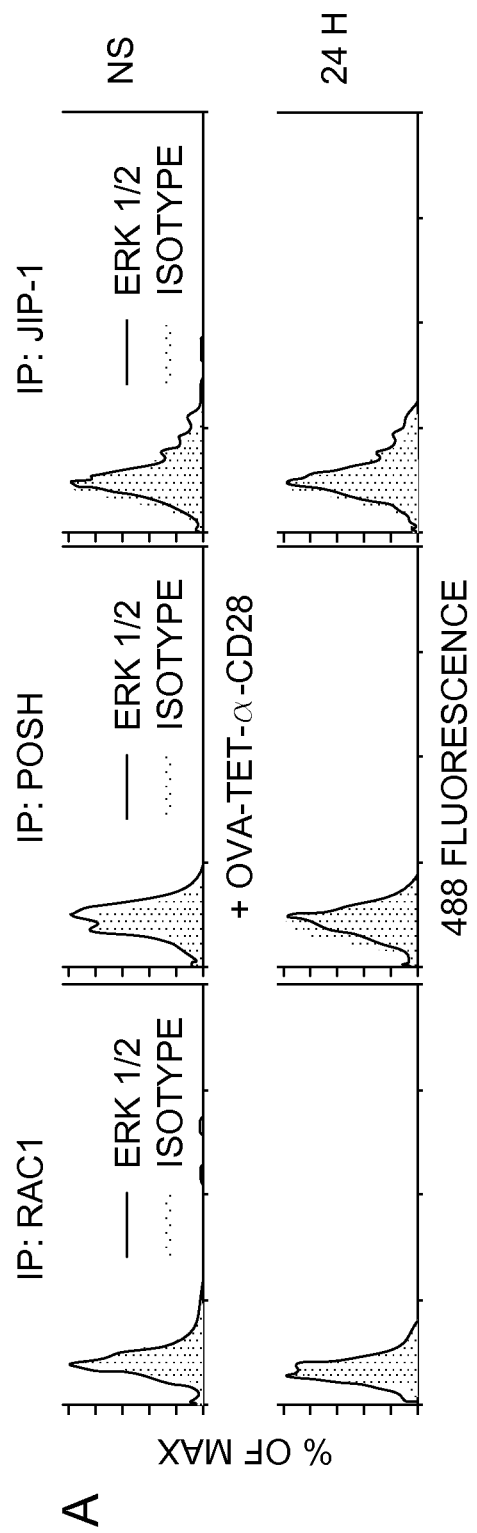
FIGS. 6(A) to 6(D) demonstrate IP-FCM quantification controls and Tat-POSH inhibitor specificity controls.
Figure 6B:
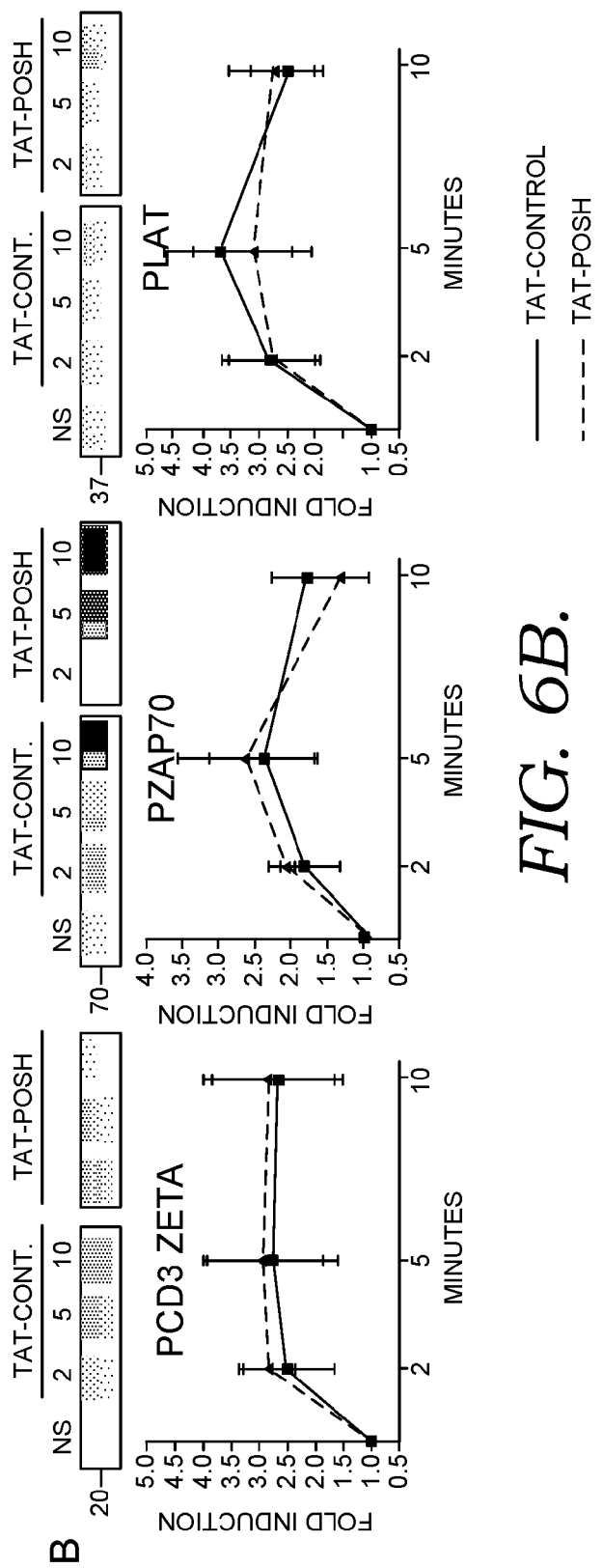
Figure 6C:
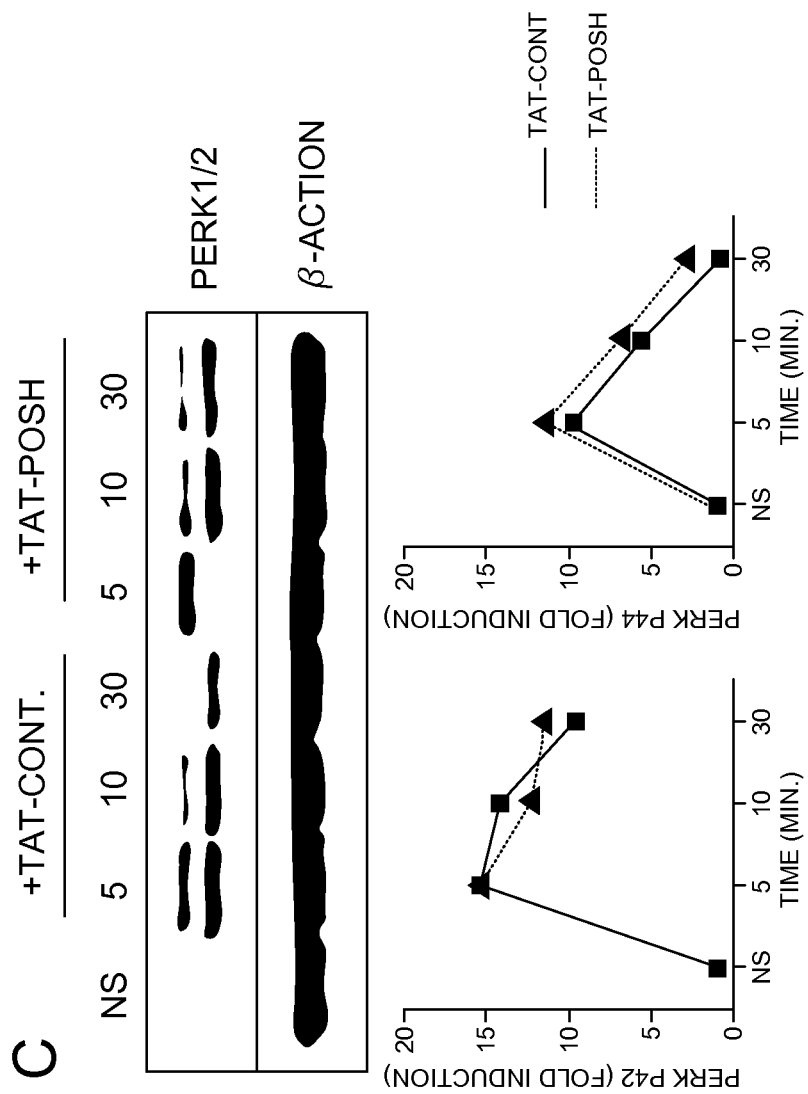
Figure 6D:
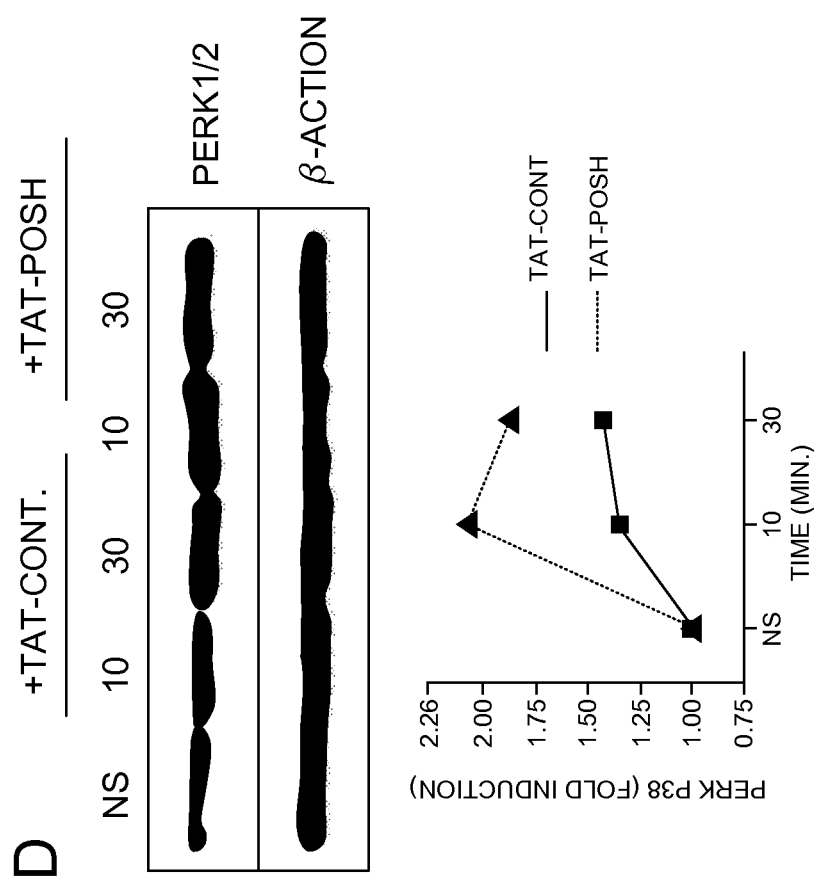
Figure 7A:
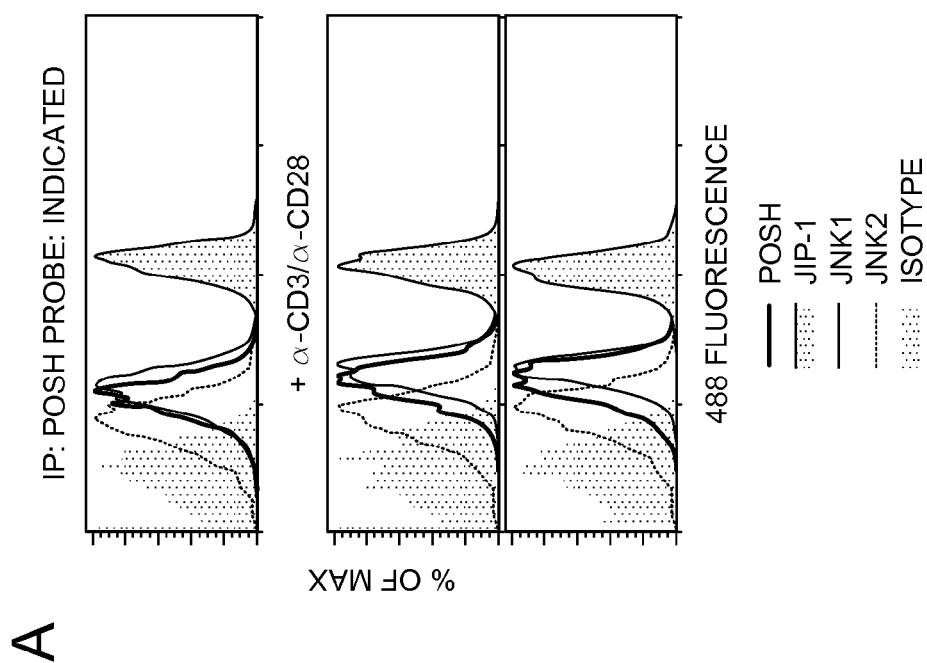
FIGS. 7(A) to 7(D) demonstrate POSH scaffold interactions in CD4$^+$ T cells.
Figure 7B:
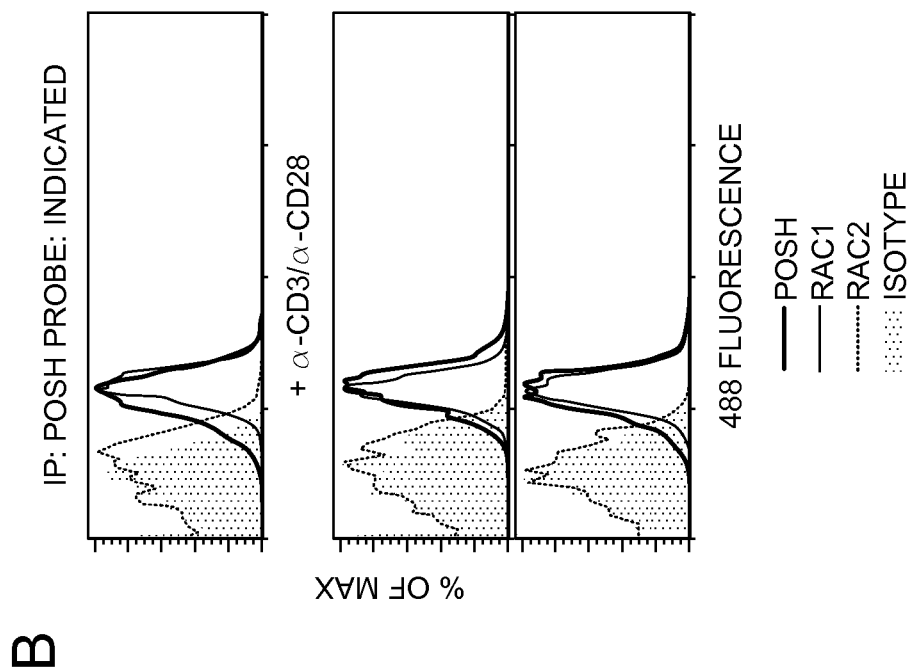
Figure 7C:
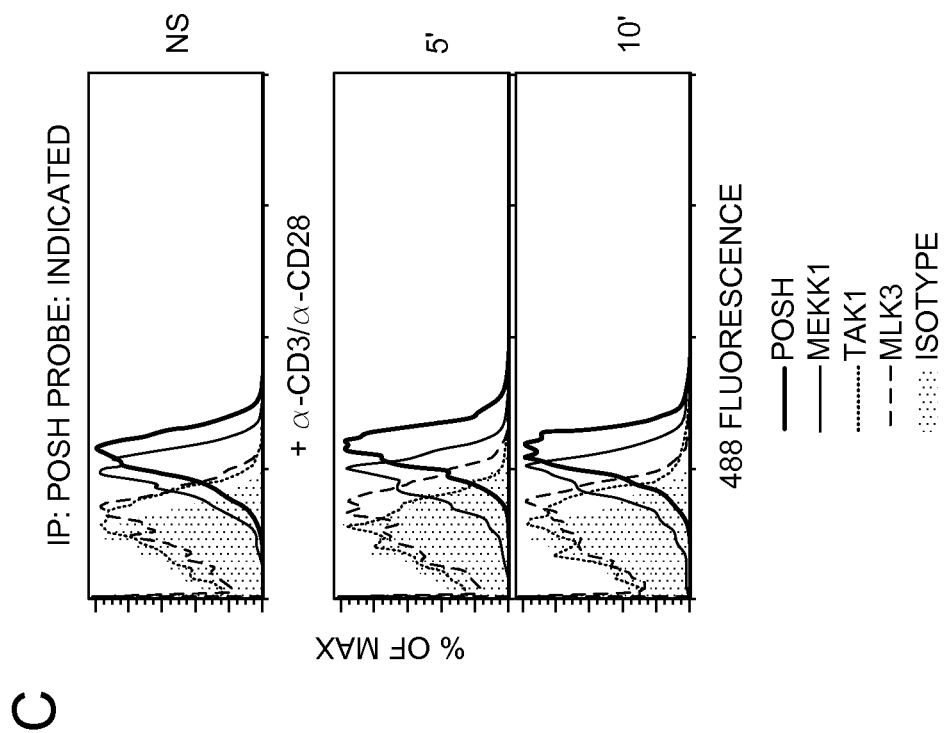
Figure 7D:
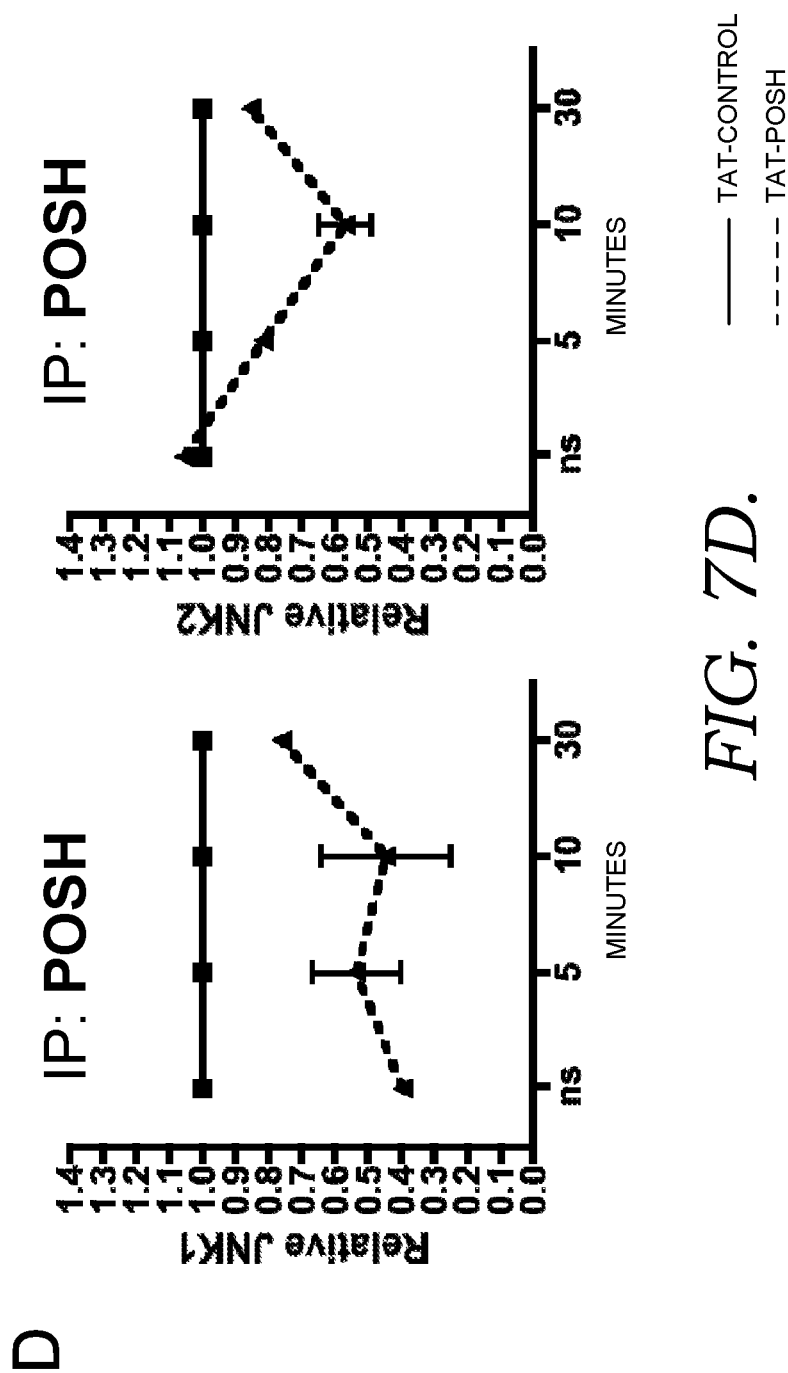

Rac1 associated with POSH and JIP-1, corroborating observations by conventional Co-IP (FIG. 5C). IP-FCM with α-POSH beads also contained significant amounts of the JNK scaffold, JIP-1 (FIG. 5D). Interestingly, when precipitating with POSH, JNK1 association increased upon activation. By contrast, JNK2 levels were not induced above background (FIG. 5D). Importantly, JNK2 was only found when precipitating with α-JIP-1 beads (FIG. 5E). Thus, these data show that POSH, JIP-1 and JNK1 are found in a shared complex and indicate a potential role for POSH in the regulation of JNK1 signaling in mature CD8+ T cells.

Experimentally, to show that the scaffold protein POSH binds JIP-1 and JNK in CD8+ T cells, OT-I blasts were stimulated with OVA-Tet/α-CD28 for the times shown in FIG. 5A. Lysates were incubated with α-Rac1 protein A/G beads. Associated proteins were assessed by immunoblot. Gst-PAK glutathione beads were used to pull down GTP-Rac-1 (active). Graph in FIG. 5B shows induction pJNK (WCL) normalized to actin loading control and the association of POSH and pJNK (IP) (relative to Rac-1) normalized to non-stimulated control. Increases over time were significant for all curves, p<0; Anova. Data shown are representative of 6 independent experiments. In FIG. 5C-5E, OT-I cells were stimulated with OVA-Tet/α-CD28 for 24 and 48 hours and lysates were subjected to IP-FCM using (C) α-Rac1, (D) α-POSH, or (E) α-JIP-1 CML beads. Red histogram represents primary analyte and is shown to serve as a bead loading control. All of the associations were significantly above isotype and negative control antibody (p<0.05) with the exception of JNK2 using α-POSH beads (FIG. 5D). In FIG. 5C-E, data shown are representative of ≥5 independent experiments.

To test for POSH scaffold interactions in CD4+ T cells, purified CD4+ T cell blasts were stimulated with α-CD3/α-CD28 for 5 or 10 min and subjected to IP-FCM analysis using α-POSH CML beads (FIG. 7). IP was confirmed by comparing the levels of POSH (primary analyte) to an Isotype control. The levels of interacting JIP-1, JNK1, JNK2, Rac1, and Rac2 were then determined. Data representative of >4 independent experiments. (B) Purified CD4+ T cell blasts were pre-treated with 20 μM Tat-cont. or Tat-POSH and stimulated with α-CD3/α-CD28 for 5 or 10 min. The levels of interacting JNK1 and JNK2 were determined relative to Tat-cont. treated cells (FIG. 7). In FIG. 7, data representative of 2 independent experiments.

Figure 8A:
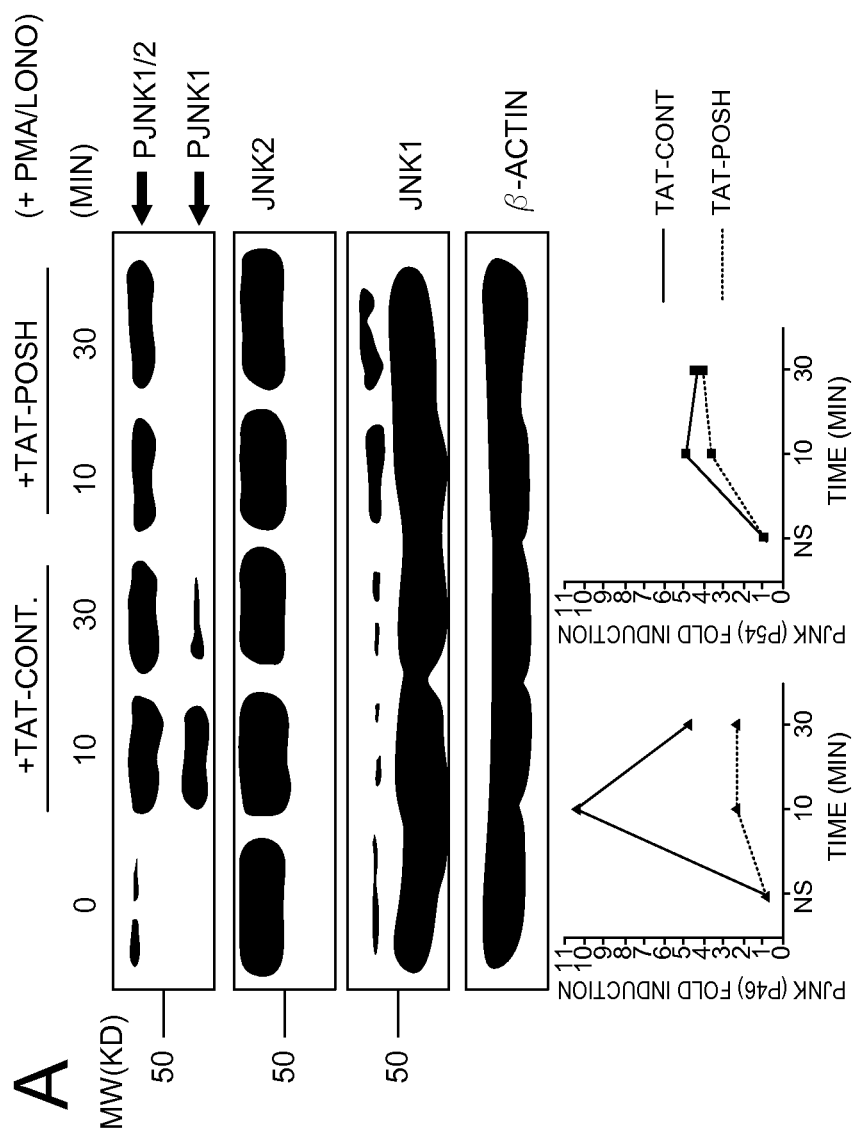
FIGS. 8(A) to 8(E) illustrate how the POSH/JIP-1 network specifically regulates JNK1 activation.
Figure 8B:
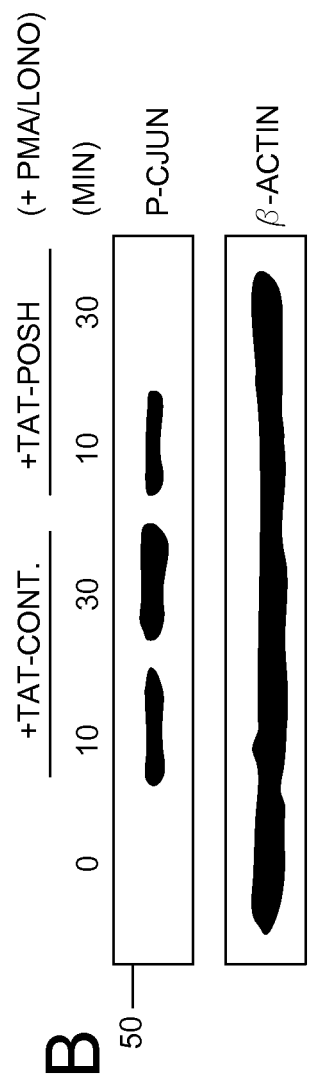
Figure 8C:
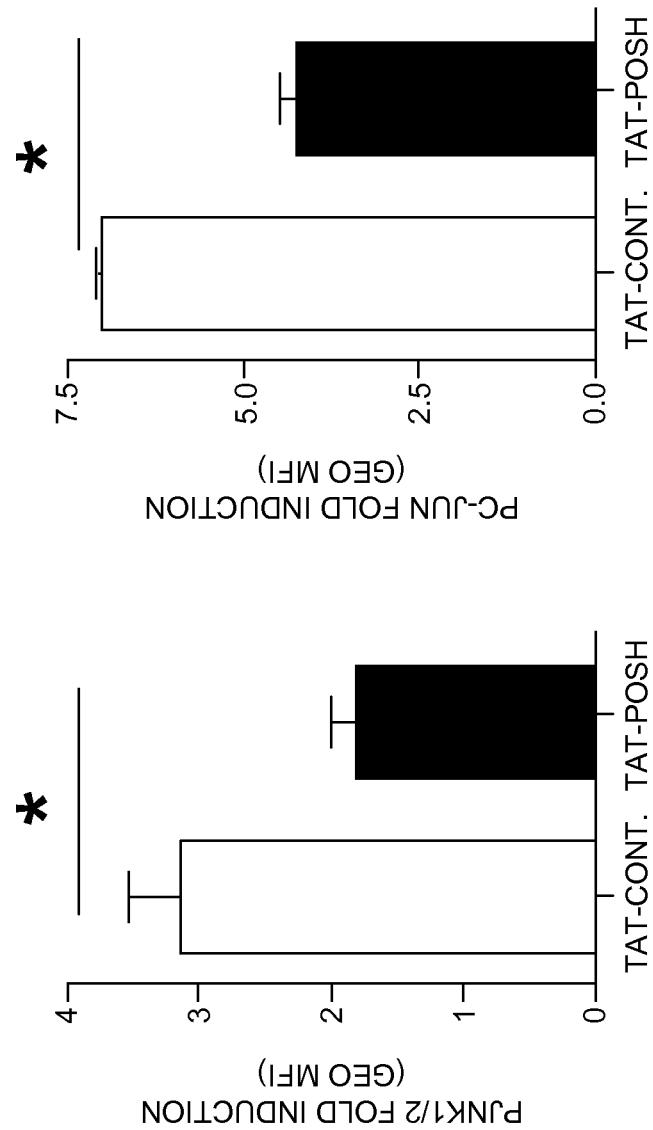

To show that the POSH/JIP-1 network specifically regulates JNK1 activation, OT-I T cells were stimulated with PMA/ionomycin in the presence of Tat-cont. or Tat-POSH peptide and lysates were subjected to immunoblot analysis with antibodies against pJNK, JNK1, JNK2 and β-actin. Graphs in FIG. 8A show induction of p-JNK for blot shown against non-stimulated control. OT-I T cells with PMA/ionomycin in the presence of Tat-cont. or Tat-POSH peptide and the level of p-cJUN induction was measured by immunoblot, with β-actin shown as a loading control Immunoblots are representative of n≥4 independent experiments (FIG. 8A-8B). In FIG. 8C, OT-I T cells were stimulated with OVAp-pulsed APCs in the presence of Tat-cont. or Tat-POSH peptide. The induction of pJNK (left) and p-cJUN (right) over a naïve control were determined by flow cytometry at 24 hours post-stimulation. Data are shown as mean±SD and are representative of n>5 independent experiments.* 2-tailed Student t test. As in FIG. 2D, OT-I T cells were pre-treated with Tat-cont. or Tat-POSH and stimulated with OVA-Tet for 30 minutes. The cells were then stained with RelA (p65) and Draq5 to identify the nucleus and analyzed by confocal microscopy (n≥39 cells). Graph represents the percentage of cells that translocate RelA to the nucleus. While in FIG. 8E OT-I T cells were stimulated with OVA-Tet/α-CD28 in the presence of Tat-cont. or Tat-POSH peptide. Cells were then lysed and subjected to IP-FCM using α-JIP-1 or α-Rac1 beads and the relative levels of POSH or JIP-1 were determined. The proposed model for the POSH/JIP-1 scaffold complex in CD8$^+$ T cells is shown. Graphs depict mean±SD of ≥3 independent experiments. *p<0.05; 2-tailed Student t test.

Figure 9A:
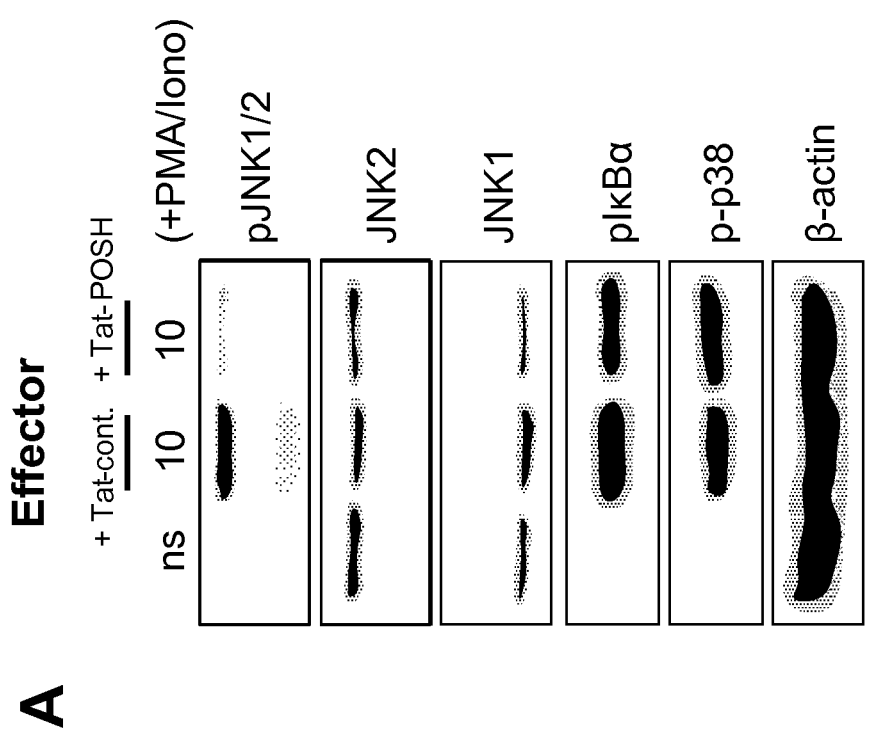
FIGS. 9(A) and 9(B) demonstrate POSH regulates JNK1/2 activation in CD4$^+$ T cells.
Figure 9B:
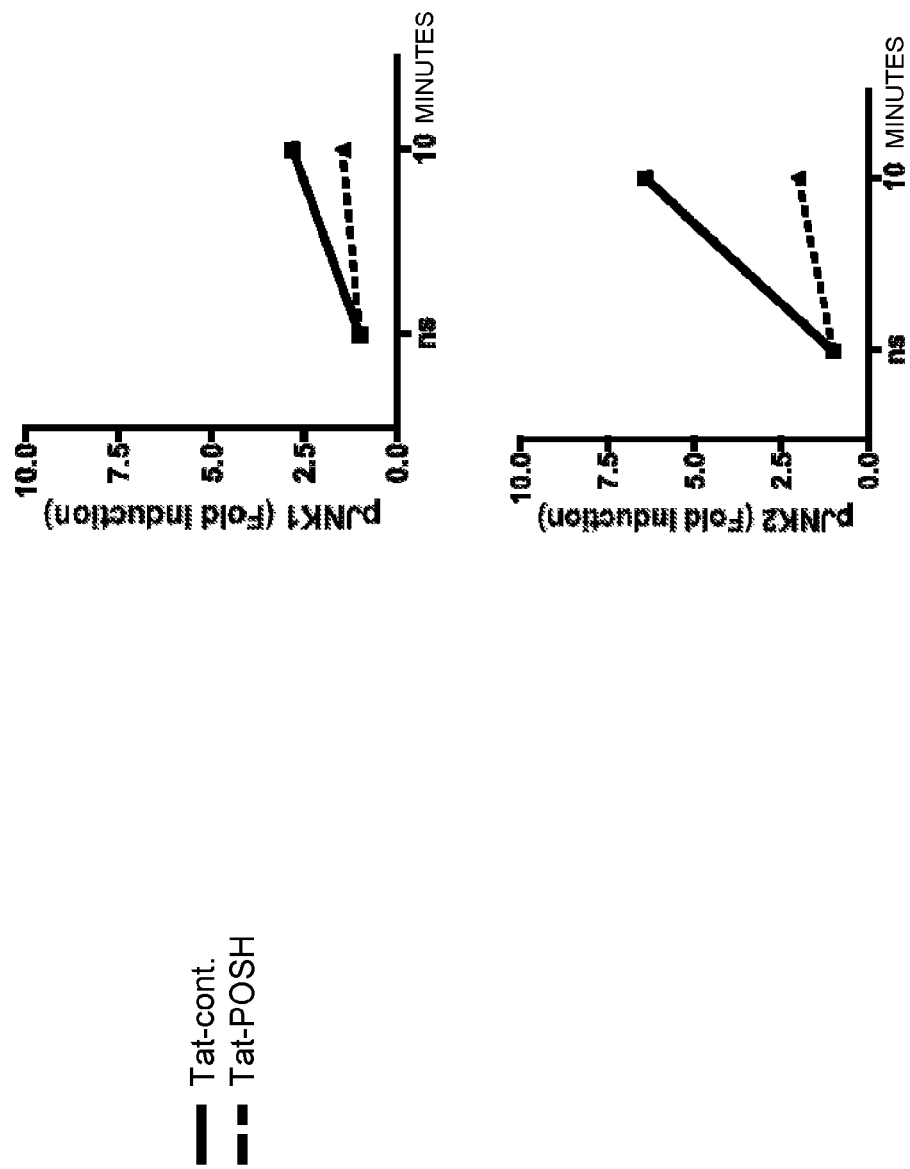

To show POSH regulates JNK1/2 activation in CD4$^+$ T cells, purified naïve CD4$^+$ T cells (left) or CD4$^+$ T cell blasts (right) were pre-treated with 20 μM Tat-cont. or Tat-POSH and stimulated with PMA/Ionomycin and the levels of pJNK1/2, JNK1, JNK2, pIκBα, p-p38, and β-actin were determined by western blotting (FIG. 9A). In FIG. 9, data representative of 3 independent experiments. The levels of pJNK1 and pJNK2 were determined by densitometry for the blots of CD4$^+$ T cell blasts as shown in FIG. 9B.

Figure 8D:
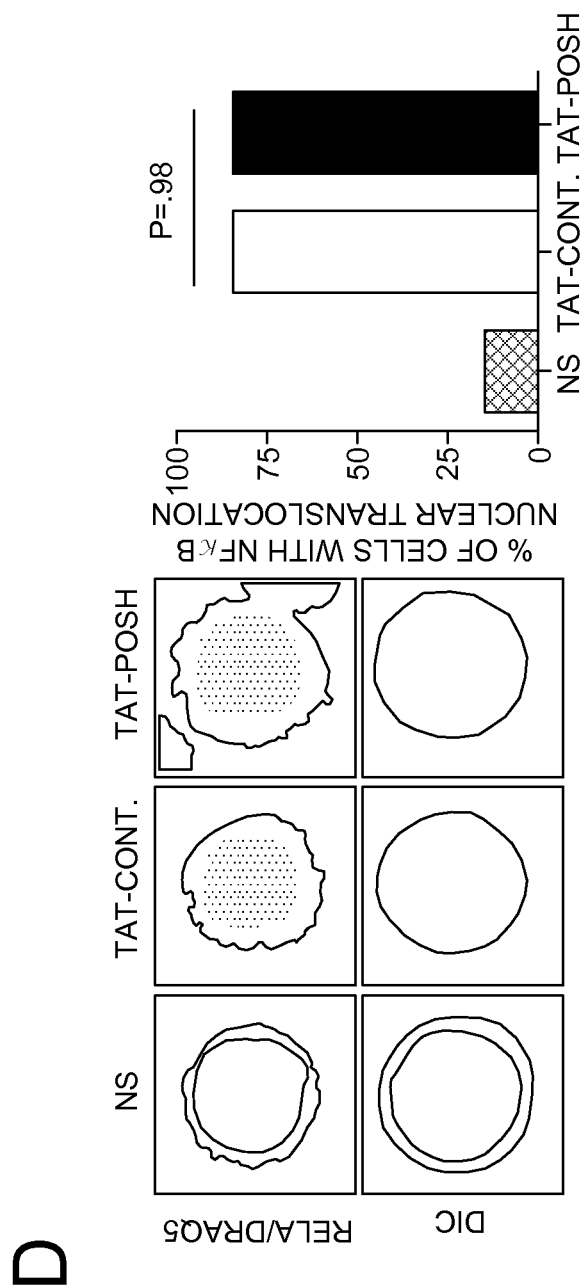
Figure 10A:
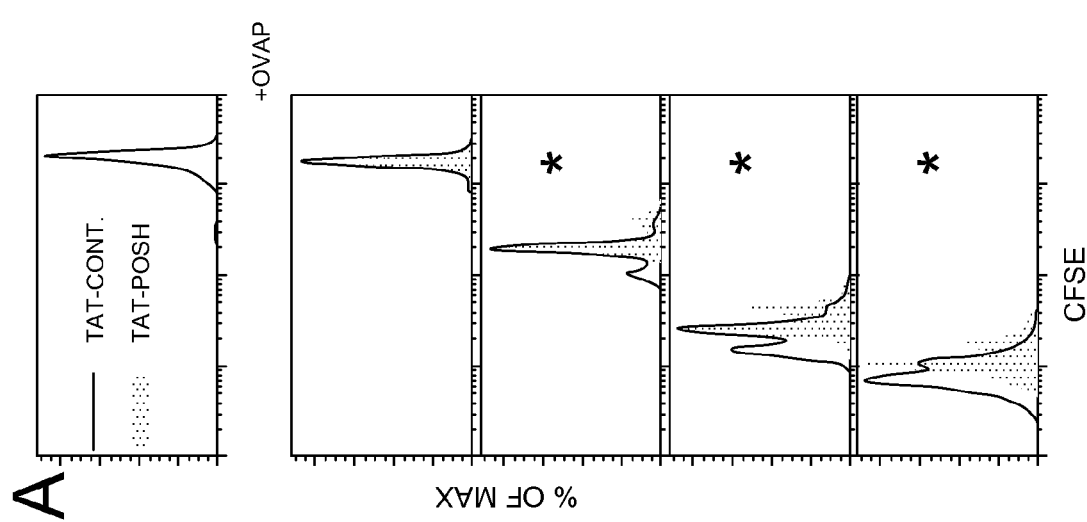
FIGS. 10(A) to 10(D) demonstrate the regulation of CD8$^+$ T-cell proliferation by the POSH/JIP-1 scaffold network.
Figure 10B:
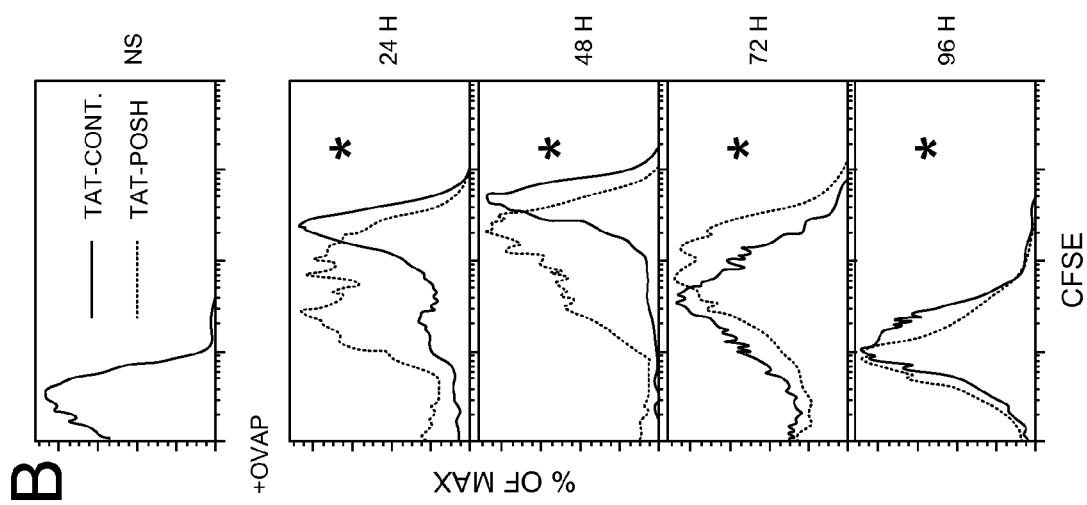
Figure 10C:
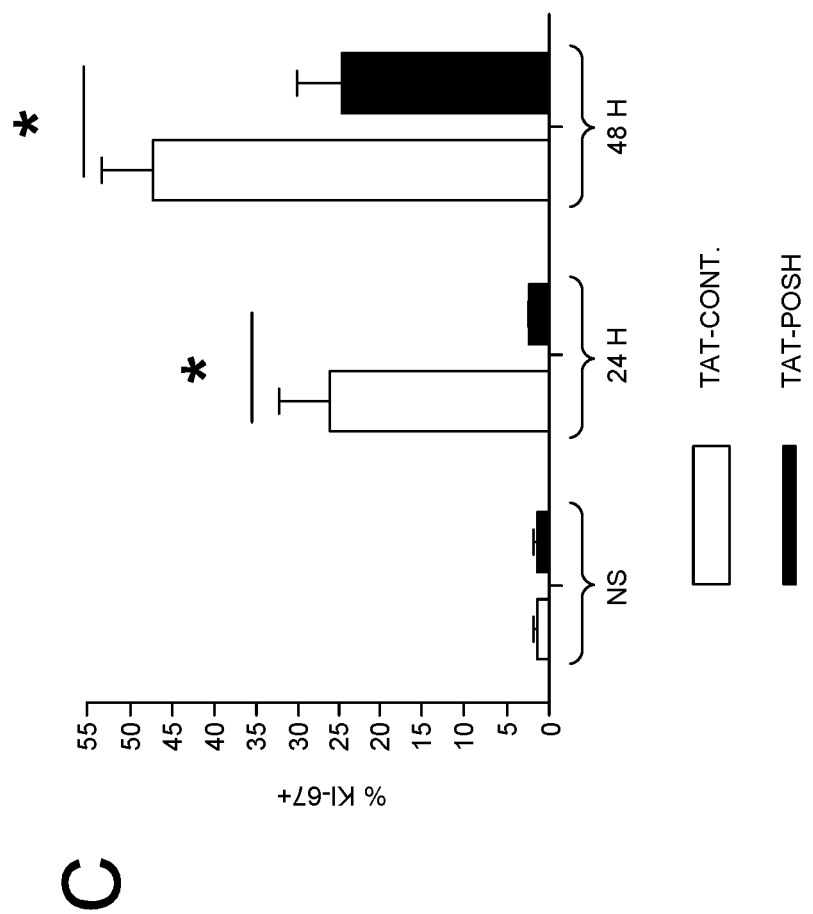
Figure 10D:
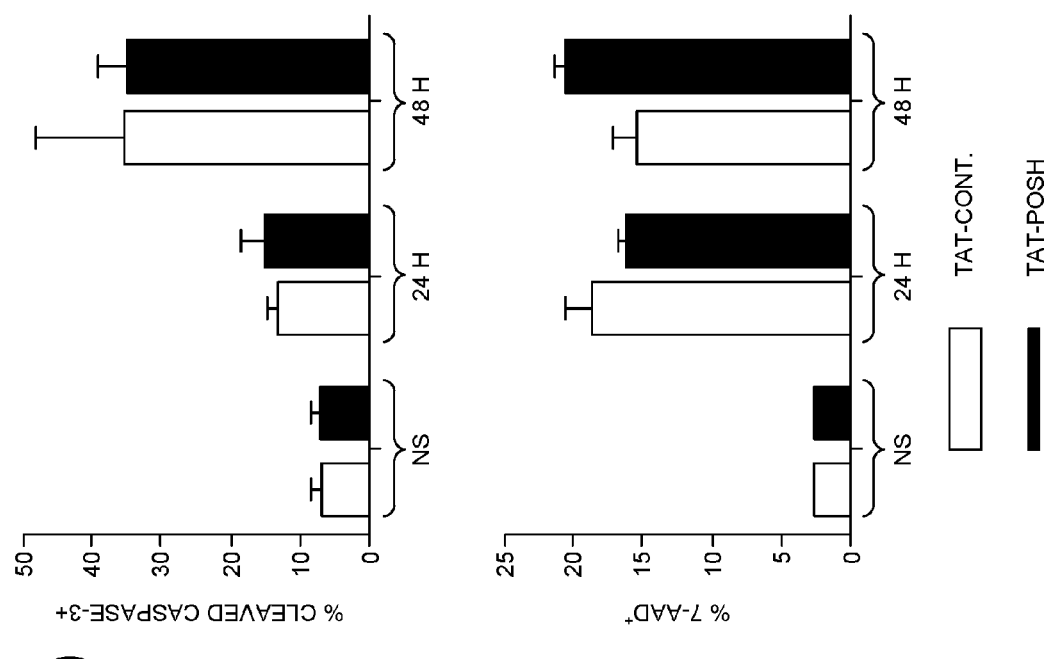
Figure 11A:
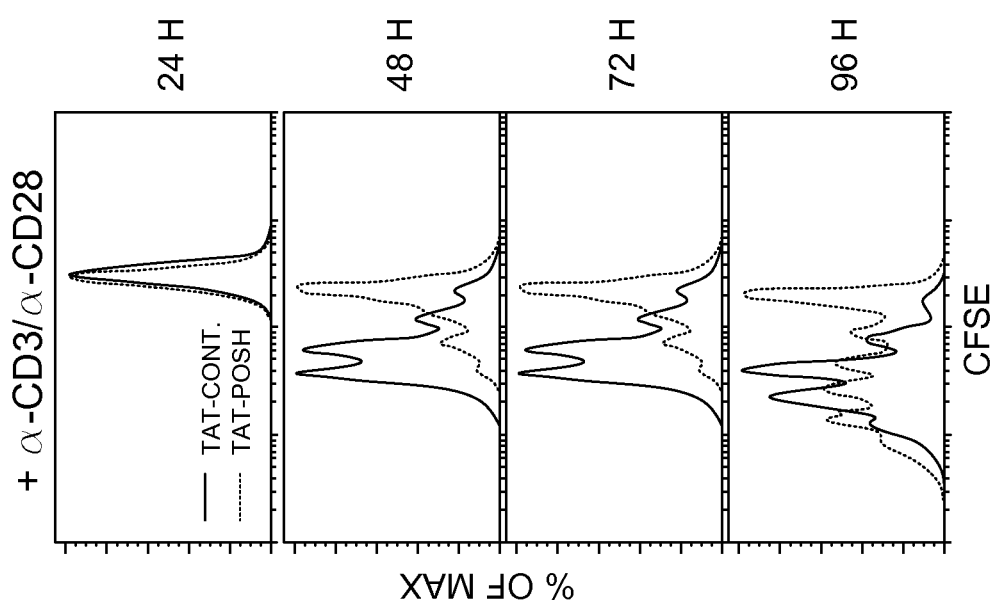
FIGS. 11(A) to 11(F) demonstrate POSH regulates cell-survival but not cell-cycle in CD4$^+$ T cells.
Figure 11B:
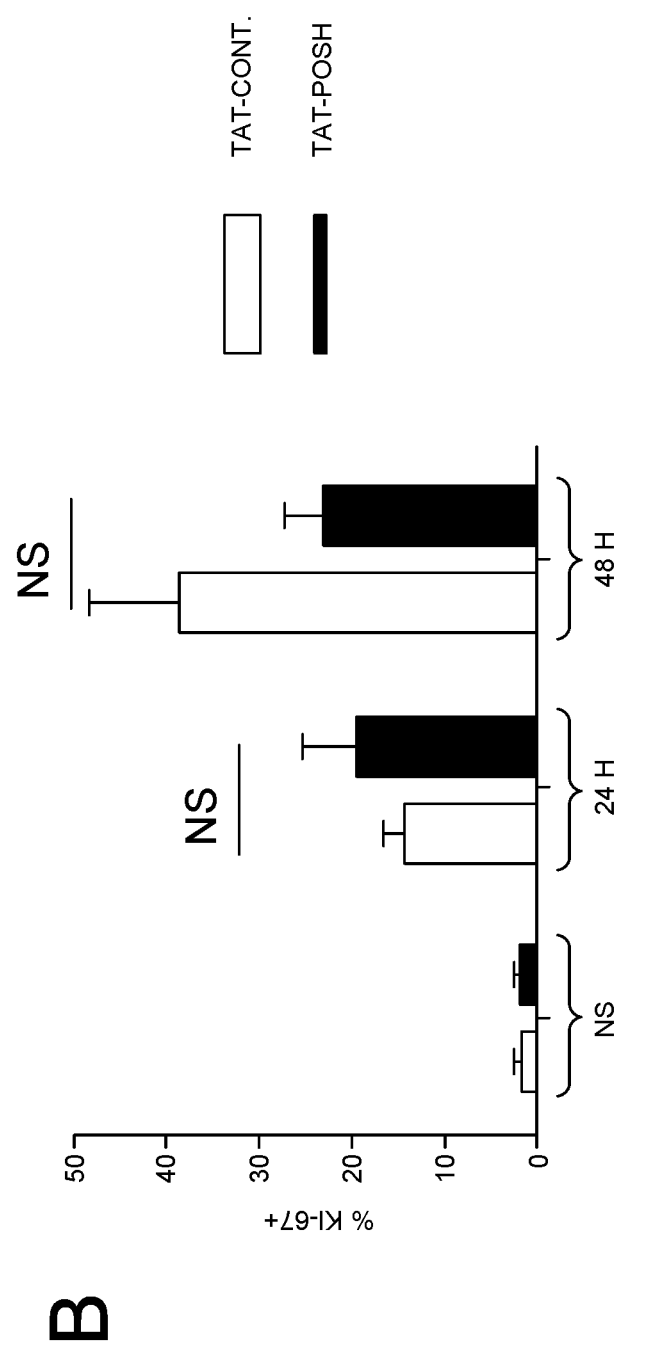
Figure 11C:
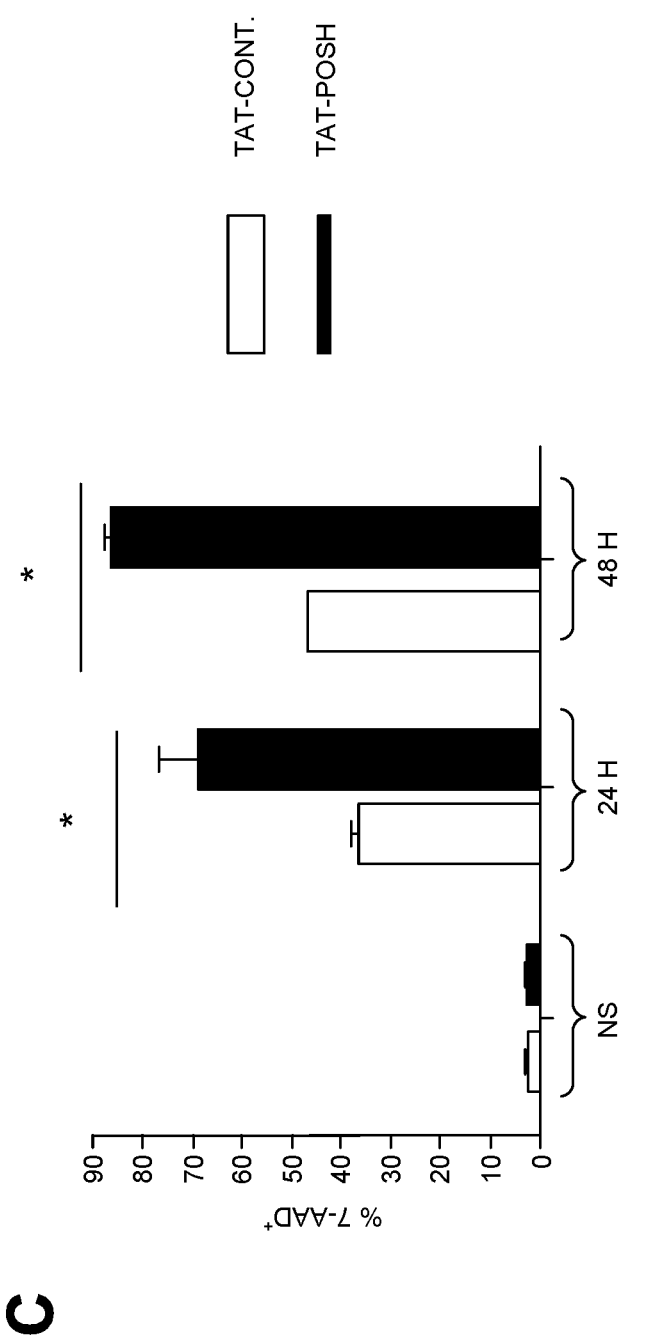
Figure 11D:
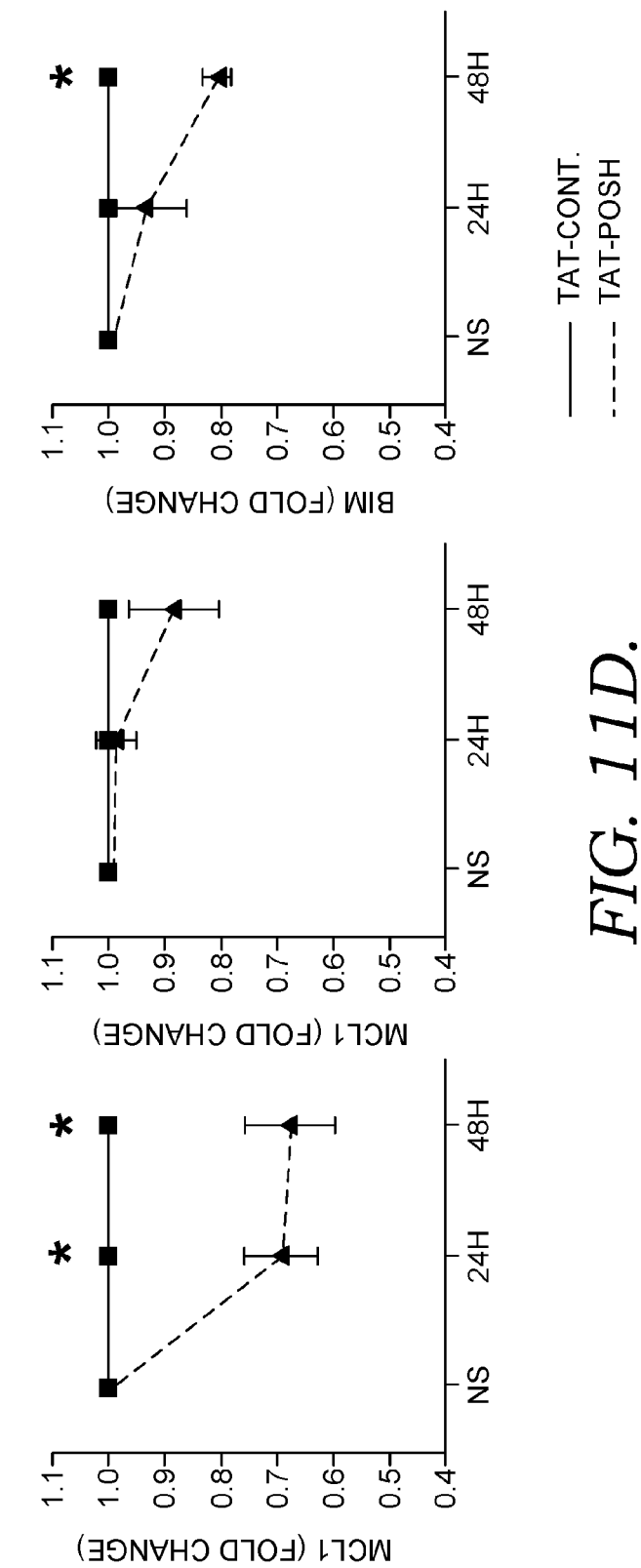
Figures 11E, 11F:
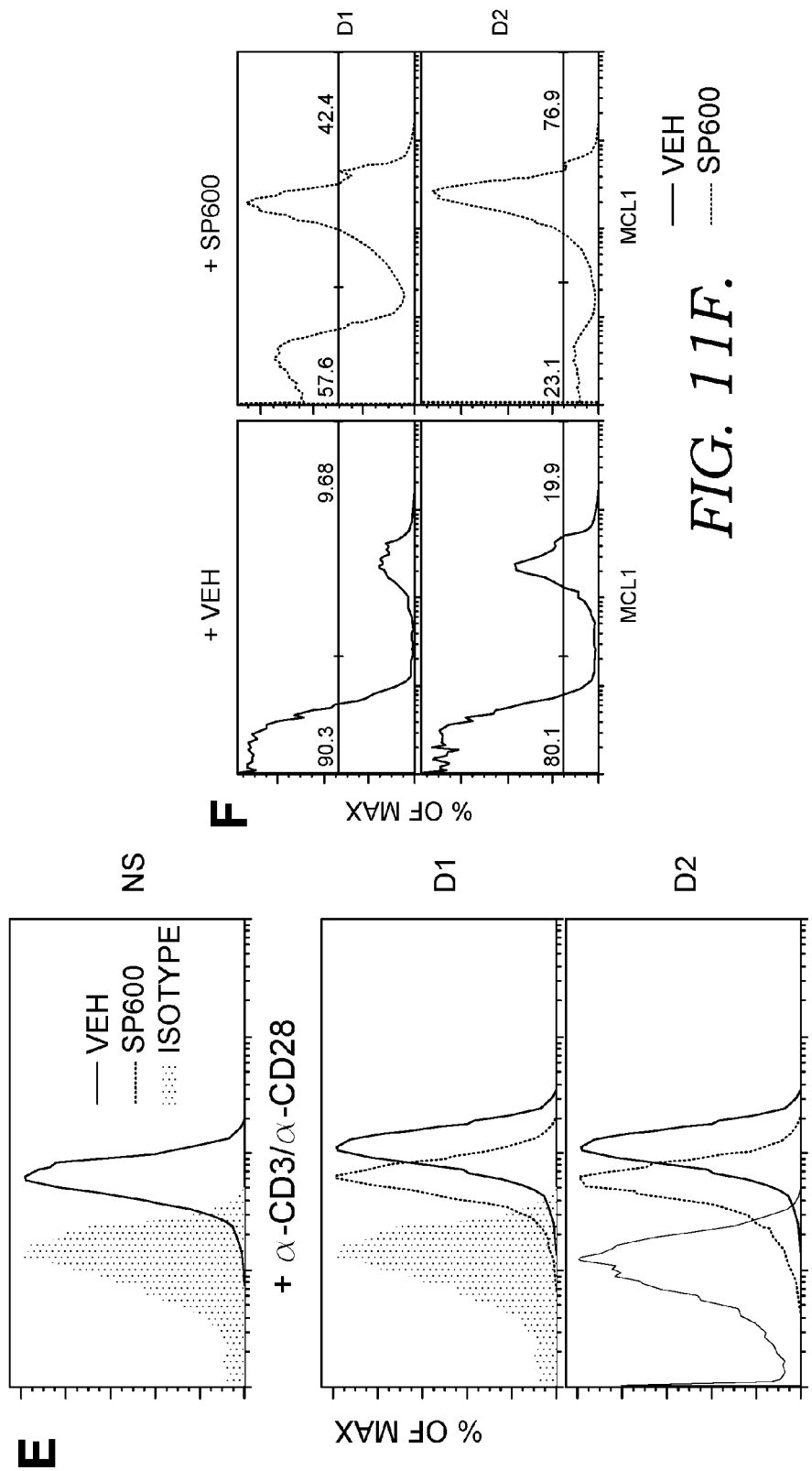

The role of the interaction between POSH and JIP-1 in the TCR-dependent regulation of JNK1 signaling was investigated. POSH is implicated in the regulation of NF-κB and has other functions that have a role in T-cell activation and differentiation. Thus, ablation of POSH expression may have secondary affects that would make the results difficult to interpret. The SH3.3 domain of POSH facilitates the interaction between POSH and JIP-1 in neurons. Therefore, to disrupt the interaction of POSH and JIP-1 we generated a cell-permeable peptide containing the HIV Tat protein transduction domain fused to the SH3.3 of POSH (Tat-POSH). This peptide was non-toxic to T cells across a large range of concentrations and was evenly distributed among cells in treated cultures (FIG. 10D, data not shown). We stimulated OT-I T cells with PMA/ionomycin or OVA-Tet/α-CD28 in the presence of Tat-POSH or control peptide. The levels of pJNK were determined by immunoblot or flow cytometry. Remarkably, phosphorylation of the 46KD JNK1 band was profoundly reduced regardless of the stimulation or time point, while the phosphorylation of JNK2 was unaffected (FIG. 8A, C). The reduction in JNK1 activation also resulted in significant reduction in the phosphorylation of the transcription factor c-JUN, a known target of active JNK1 (FIG. 8B-C). Even though the domain of POSH known to induce NF-κB translocation overlaps with the SH3.3 domain, Tat-POSH did not affect NF-κB nuclear translocation, indicating POSH SH3.3 is not involved in regulating NF-κB signaling (FIG. 8D). Finally, Tat-POSH had minimal effect on the phosphorylation of CD3, ZAP-70, LAT, ERK and p38 MAPK (FIG. 6). Collectively, these data indicate the specificity of the inhibitor and reveal that inhibition through the POSH SH3.3 domain solely affects JNK1 signaling in T cells.

Figure 8E:
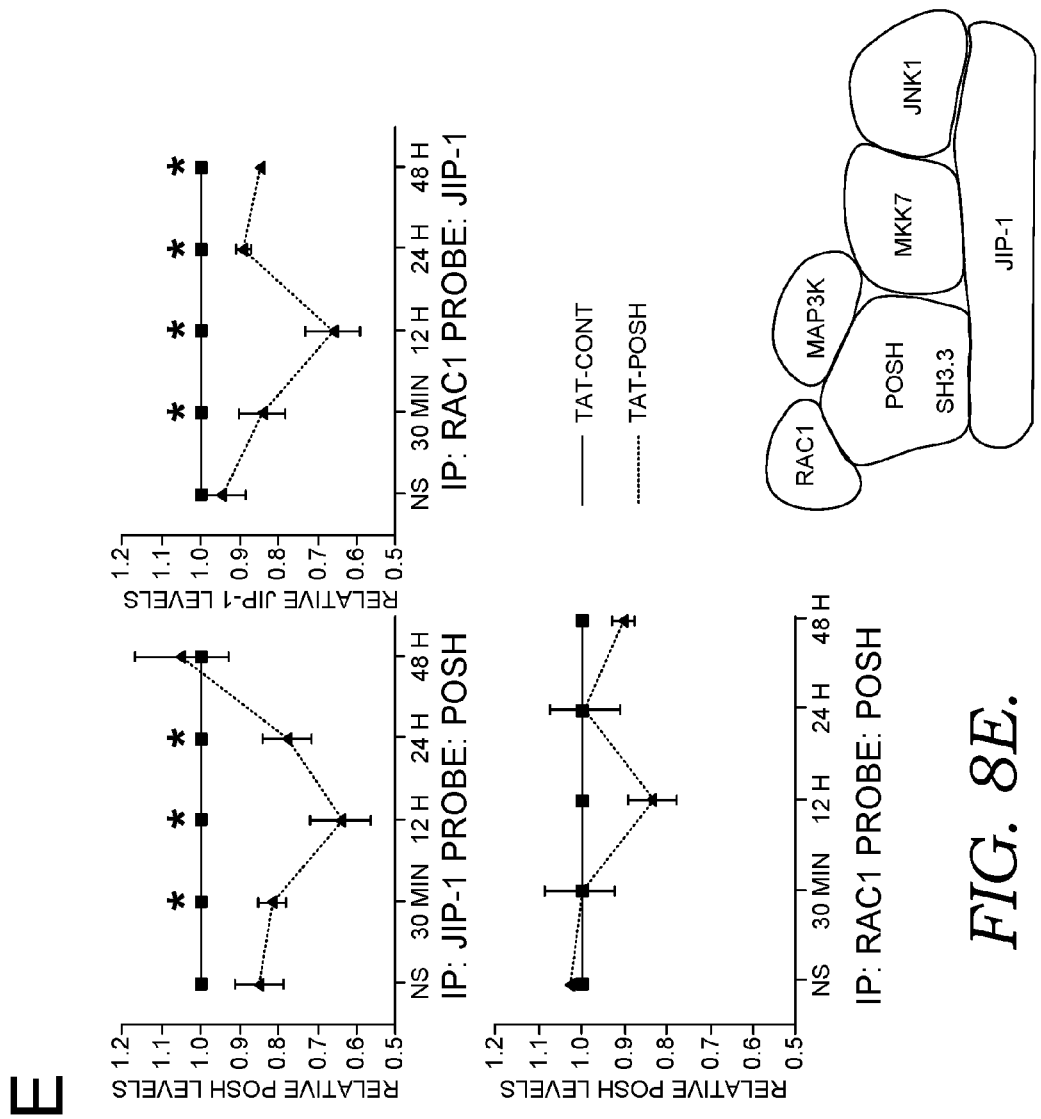
Figure 12A:
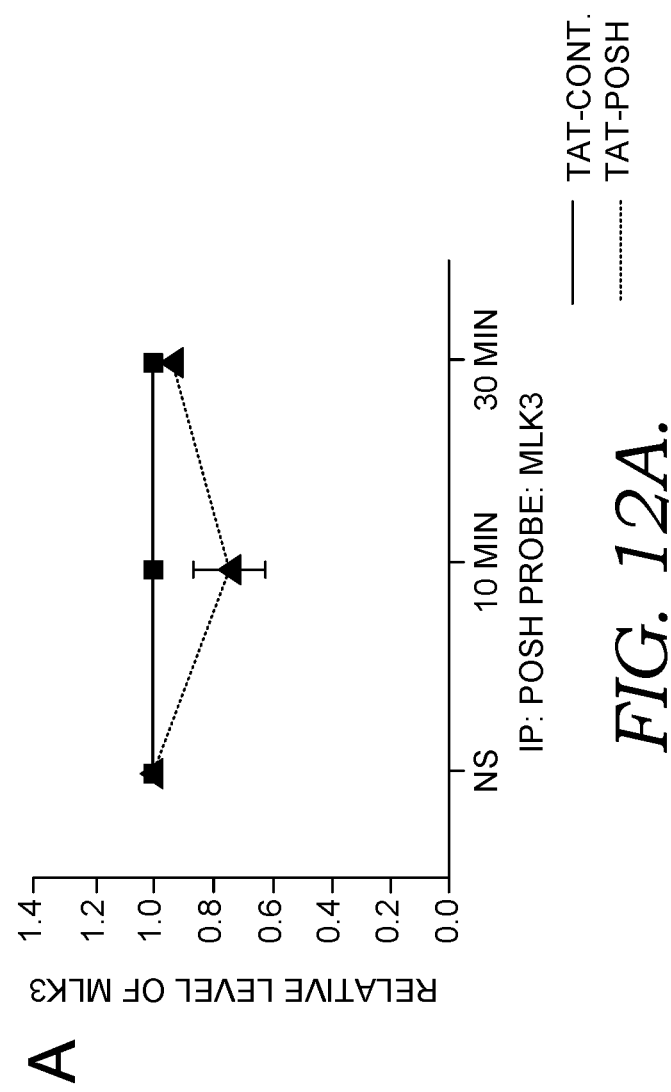
Figure 12C:
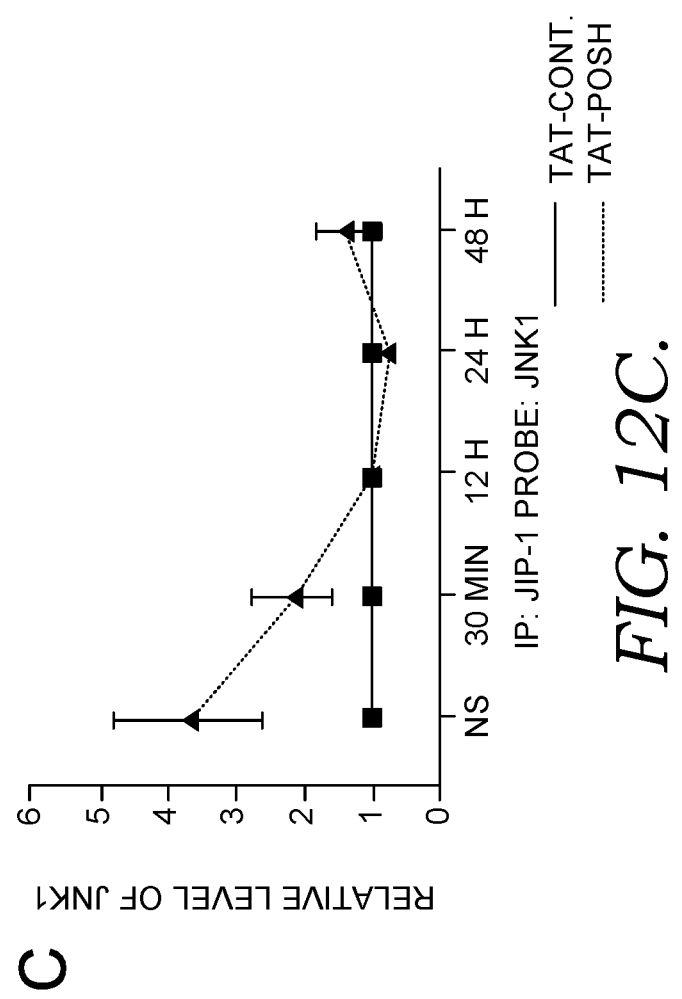
Figure 12D:
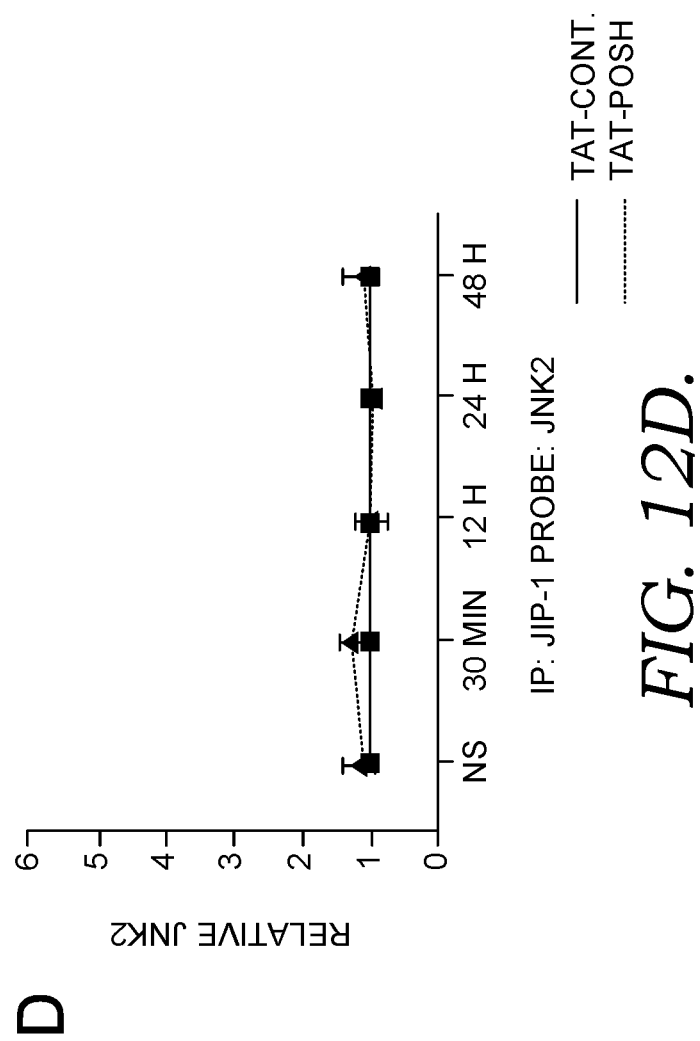
Figure 12E:
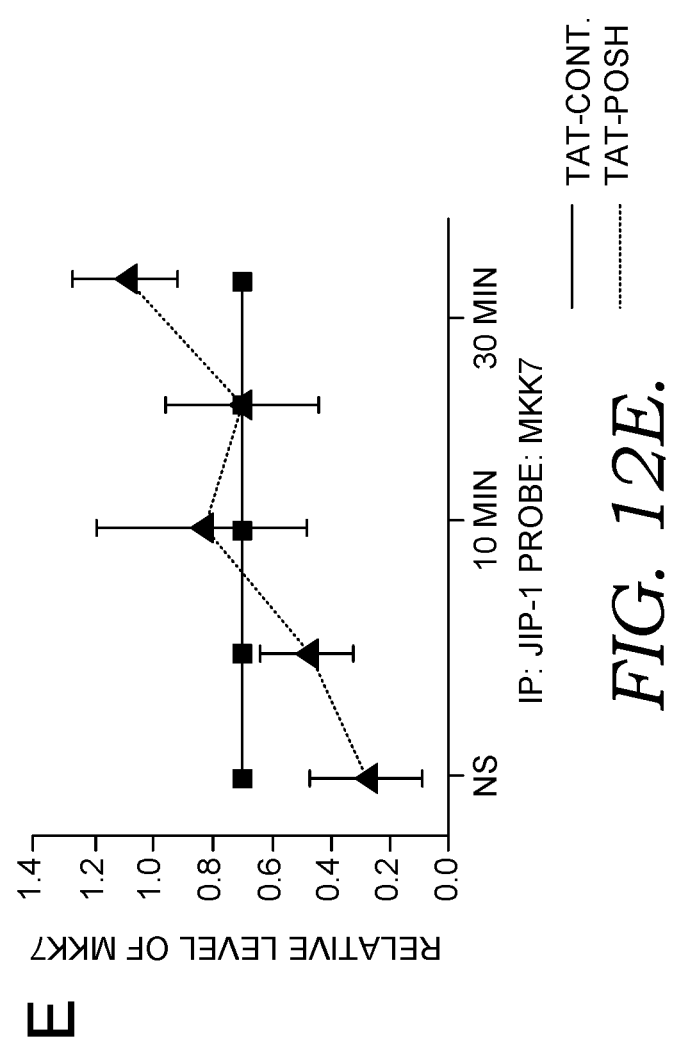

Next, IP-FCM analyses of lysates from T cells stimulated in the presence of Tat-POSH were performed to map the composition of the POSH/JIP-1 scaffold complex. Tat-POSH disrupted approximately 30% of POSH/JIP-1 complexes over the first 48 hours of stimulation (FIG. 8E). In the presence of Tat-POSH, Rac-1, the MAP3K proteins, MLK-3 and Tak1, were not significantly reduced in Co-IP with POSH, while MKK7 and JNK1 were not affected in Co-IP with JIP-1 (FIG. 8E, FIG. 12). To determine the configuration of the POSH/JIP-1 scaffold complex, OT-I T cells were stimulated with PMA/ionomycin (FIG. 12A-B) or OVA-Tet/α-CD28 (FIG. 12C-E) in the presence of Tat-cont. (solid lines) or Tat-POSH peptide (dashed lines). Cells were then lysed and subjected to IP-FCM using (FIG. 12A-B) α-POSH beads and the levels of (A) MLK-3 and (B) MKK7 were determined. In FIG. 12C-12E, lysates were precipitated with α-JIP-1 beads and the levels of (C) JNK1, and (D) JNK2 and (E) MKK7 were analyzed. Graphs of FIG. 12, depict mean±SD of ≥3 independent experiments (*indicates p<0.05, the rest of the differences are not significant. This suggests POSH binds Rac-1 and MLK-3 and the SH3.3 domain of POSH associates with the JIP-1/MKK7/JNK1 complex to assemble the JNK1 signaling module in CD8$^+$ T cells (FIG. 8E).

The POSH/JIP-1 Scaffold Complex Regulates Proliferation and Effector Function.

JNK1 is important for CD8$^+$ T-cell proliferation, regulates entry into cell cycle and plays a major role initiating apoptosis. First we determined the effect of un-coupling POSH from JIP-1 on proliferation. Naïve OT-I T cells stimulated with OVAp-pulsed APC in the presence of Tat-POSH exhibited significant reduction in the number of divisions (FIG. 10A). T cells stimulated in the presence Tat-POSH had reduced induction of CD25 (FIG. 10B). Importantly, this defect was not recovered in the presence of excess IL-2 and/or IL-12 (data not shown). Next, we determined whether these defects in proliferation were the result of fewer cells entering cell cycle or increased apoptosis. The percent of cells in cell cycle, as measured by the Ki-67, was significantly reduced in the presence of Tat-POSH (FIG. 10C). However, there was no statistical difference in the percent of cells undergoing apoptosis, as measured by cleaved caspase-3, 7-AAD or Annexin-V (FIG. 10D, data not shown). Remarkably, these data closely resemble observations from JNK1$^{-/-}$ CD8$^+$ T cells and support the role of the POSH/JIP-1 scaffold network in regulating JNK1 induced proliferation.

Experimentally, OT-I T cells were stimulated with OVAp-pulsed APCs in the presence of Tat-cont. or Tat-POSH peptide and Cell division of CD8$^+$ cells was measured by CFSE dilution (FIG. 10A) and the level of CD25 (IL-2Rα) was determined (FIG. 10B). Representative of n=5. In FIG. 10C-D, polyclonal CD8$^+$ T cells were stimulated with 1 μg/mL α-CD3 and 1 μg/mL α-CD28 in the presence of Tat-cont. or Tat-POSH and the percentage of (C) Ki-67$^+$ and (D) Cleaved Caspase-3$^+$ cells and 7AAD$^+$ cells were determined at 24 and 48 hours post-stimulation. In FIG. 10A-D, data are shown as +SD and are representative of ≥4 independent experiments. +*p<0.05; Mann-Whitney rank sum (FIG. 10A-B); 2-tailed Student t test (FIG. 10C-D).

To show that POSH regulates cell-survival but not cell-cycle in CD4+ T cells, purified CD4+ T cells were pre-treated with 20 µM Tat-cont. or Tat-POSH and stimulated with α-CD3/α-CD28 in the presence of IL-2 and cell division was determined by CFSE dilution at days 1-4 (FIG. 11). In FIG. 11, data representative of >4 independent experiments. In FIG. 11B, cells were stimulated as in FIG. 11A and the percent of Ki-67+ cells were determined at day 1 and 2. In FIG. 11C, Cells were stimulated as in FIG. 11A and the percent of apoptotic cells were determined by 7-AAD staining. In FIG. 11, data representative of 3 independent experiments, * p<0.05. In FIG. 11D, purified CD4+ T cells were stimulated as in FIG. 11 and the levels of Mcl1, Bcl2, and Bim were determined by flow cytometry on days 1 and 2. Data representative of 3 independent experiments, * p<0.05. Purified CD4+ T cells were pre-treated with Vehicle or SP600125 and stimulated with α-CD3/α-CD28 in the presence of IL-2 for 2 days and the levels of Mcl1 were determined. In FIG. 11F, cells were stimulated as in FIG. 11E and the levels of cell death were determined by 7-AAD staining at days 1 and 2.

Figure 13A:
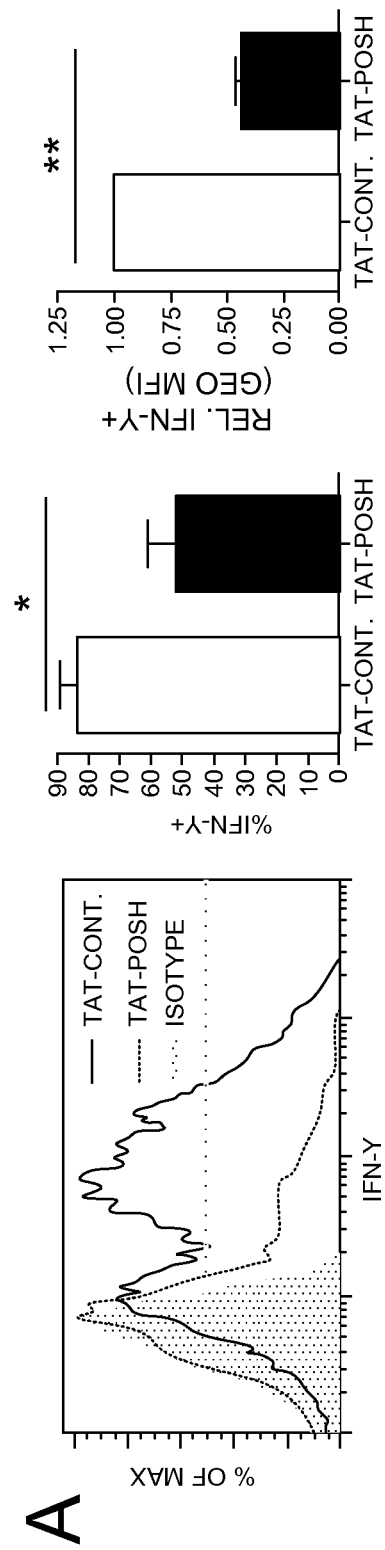
FIGS. 13(A) to 13(G) illustrate how the POSH/JIP-1 scaffold network regulates effector cytokine production.
Figure 13B:
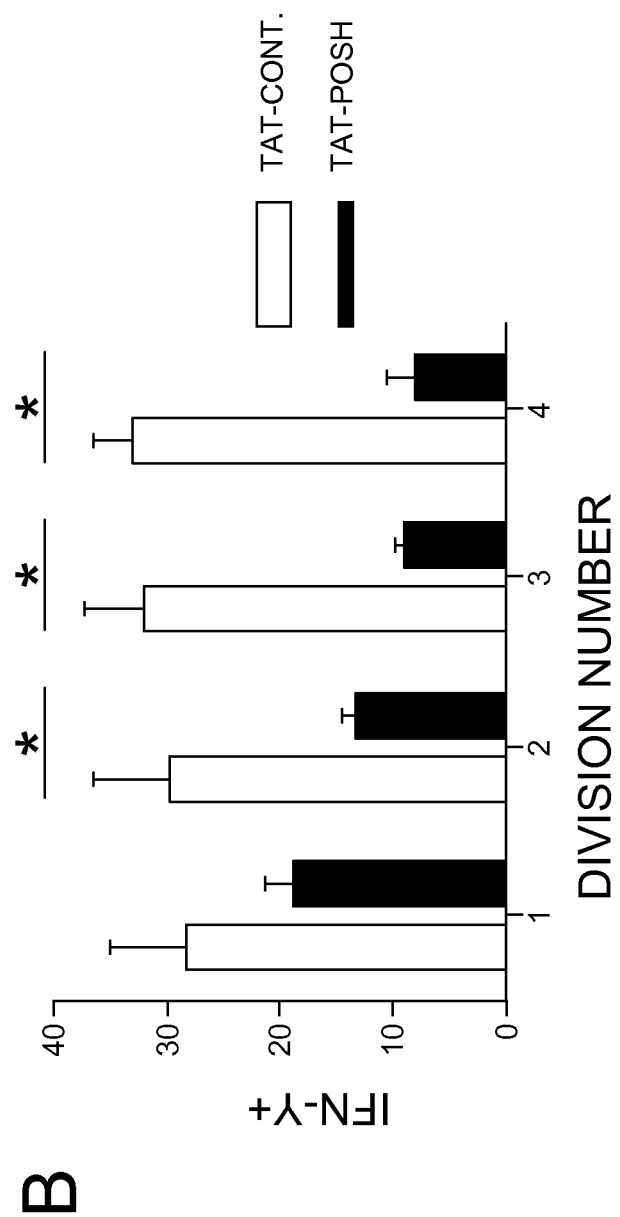
Figure 13C:
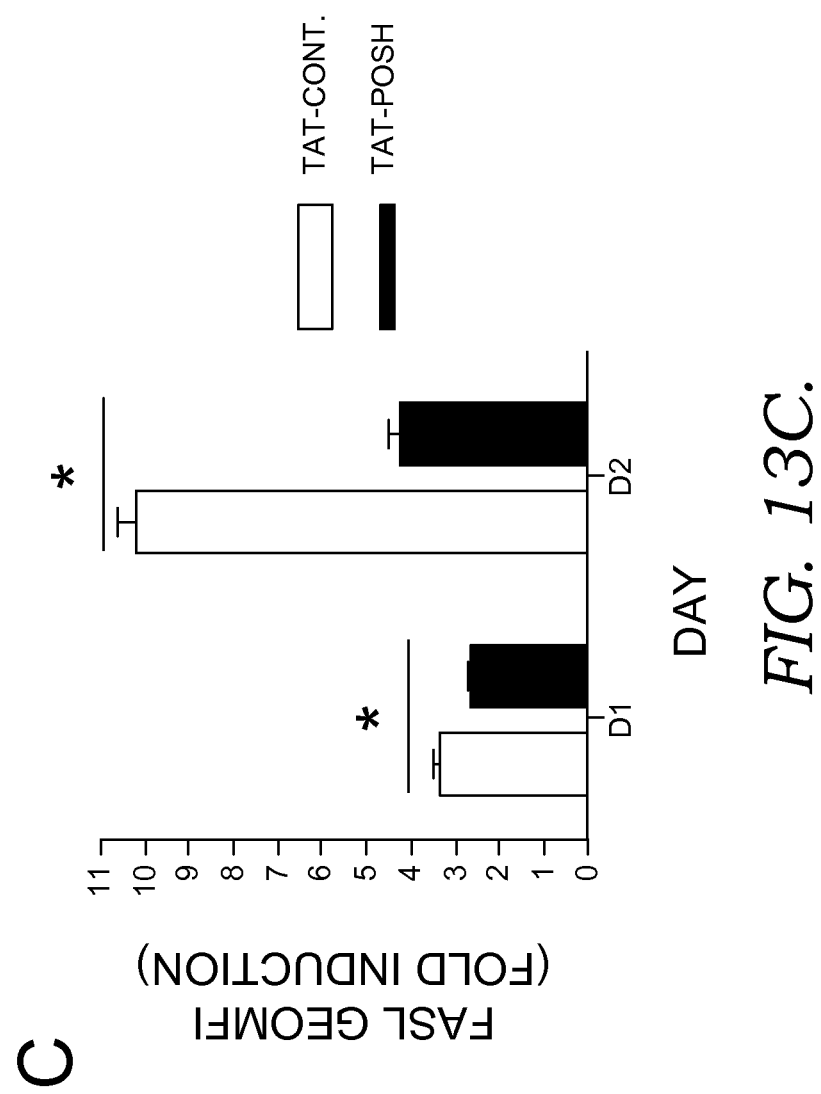
Figure 13D:
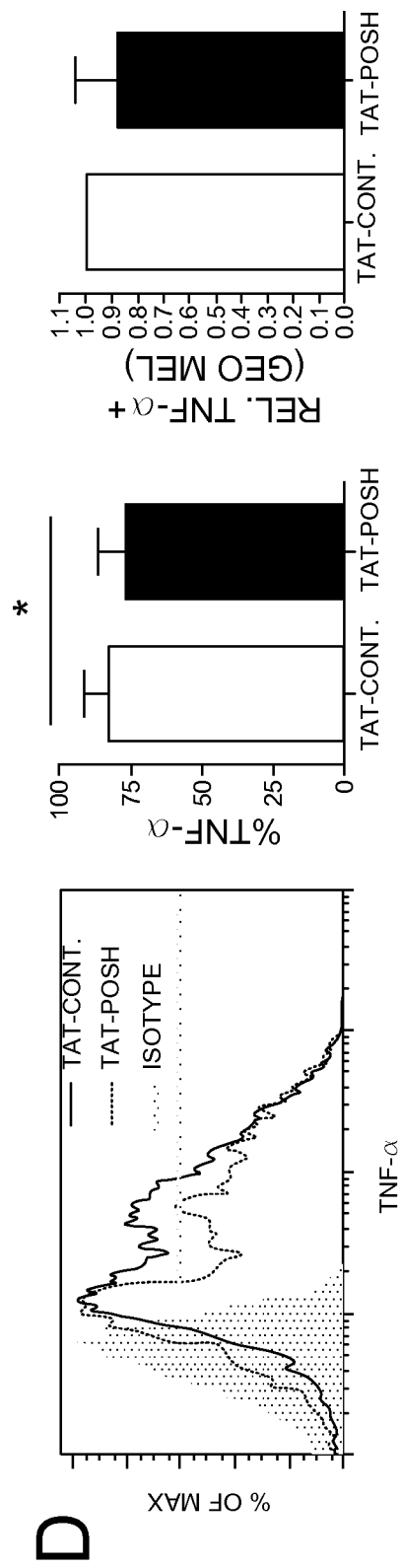
Figure 13E:
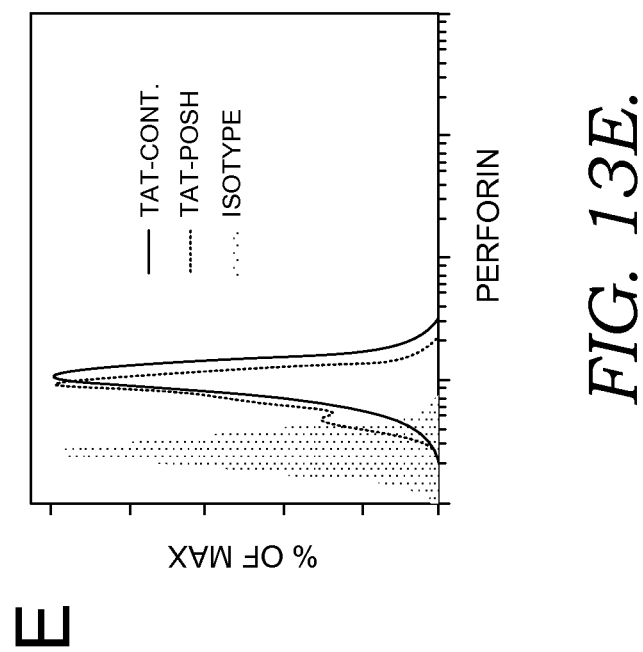
Figure 13F:
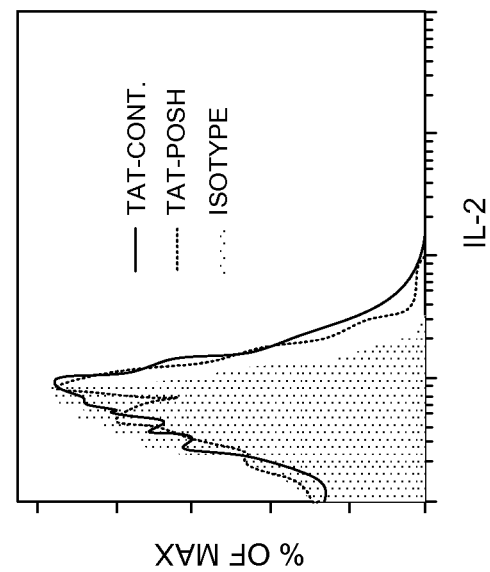
Figure 13G:
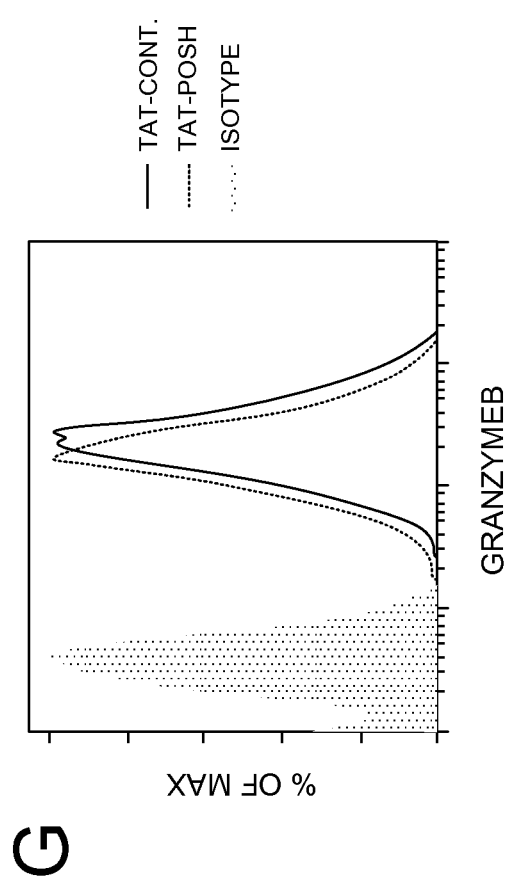

JNKs are important in the differentiation and development of effector function of CD8+ T cells. JNK1 positively regulates IFN-γ, Perforin, and TNF-α while JNK2 inhibits IFN-γ and Granzyme B induction. To test the role of the POSH/JIP-1 scaffold complex on the induction of these effector molecules, OT-I T cells were stimulated with OVAp-pulsed APC in the continuous presence of Tat-POSH or Tat-control. Four days after stimulation, cells were washed and re-stimulated in the presence of Brefeldin A (without additional Tat-POSH) and then assessed for effector molecule expression by intracellular staining. Cells initially stimulated in the presence of Tat-POSH had a significant reduction in both the percentage of IFN-γ+ cells and amount of IFN-γ produced on a per-cell basis (FIG. 13A). Importantly, this was independent of cell division as significantly fewer of even the most divided Tat-POSH treated cells produced IFN-γ (FIG. 13B). FasL induction was also significantly decreased (FIG. 13C) and there was a slight but significant reduction in the percentage of TNF-α+ cells (FIG. 13D). Conversely, the levels of Perforin, IL-2 and Granzyme B remained unchanged between Tat-POSH and control treated cells (FIG. 13E-G). Disruption of the POSH/JIP-1 complex resulted in a modest (10-15%) but significant reduction in in vitro cytotoxicity that closely resembled JNK1−/− T cells (data not shown). Together, these data indicate that the POSH/JIP-1 complex is specific for the regulation of JNK1 dependent effector function.

To test that the POSH/JIP-1 scaffold network regulates effector cytokine production, naïve OT-I T cells were stimulated with OVAp-pulsed APCs in the presence of Tat-cont. or Tat-POSH peptide for 4 days and re-stimulated with OVA-Tet in the presence of BFA for 6 hours. As shown in FIG. 13A, the percentage of IFN-γ+ T cells (left) and the amount (right) of IFN-γ produced per cell, measured by intracellular staining, was determined following re-stimulation. Cells were stained with CFSE and stimulated and stained. FIG. 13B shows the percentage of IFN-γ+ T cells for each CFSE division peak (n=3). Cells were stimulated with OVAp-pulsed APCs in the presence of Tat-cont. or Tat-POSH peptide and FasL surface expression measured by flow cytometry. In FIG. 13C, graph depicts fold induction over naïve T cells. In FIG. 13D, the percentage of TNF-α+ cells (left) and amount (right) were measured as in FIG. 13A. The expression of (E) Perforin. (F) IL-2 and (G) Granzyme B are also shown. FACS plots, in FIG. 13A, D, E-G, are representative of n≥4 independent experiments. In FIG. 13A, C-D, data are shown mean±SD representative of n≥3 independent experiments. * p≤0.05, ** p≤0.01; 2-tailed Student t test.

Tat-POSH Treated CTL Exhibit Impaired Tumor Clearance In Vivo.

Figure 14A:
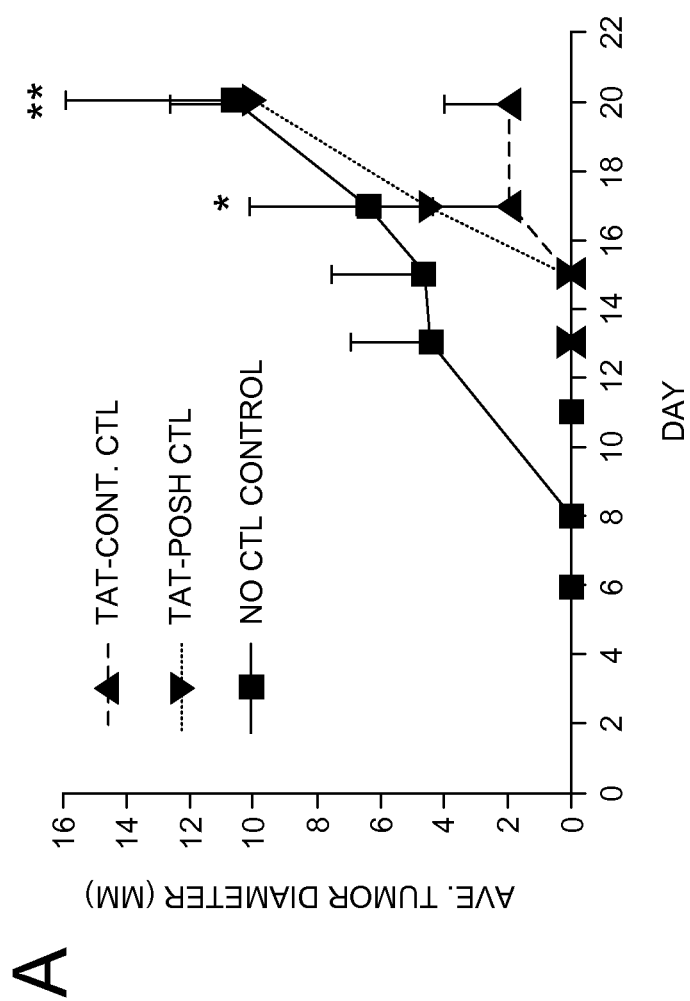
FIGS. 14(A) to 14(D) demonstrate the disruption of POSH/JIP-1 network that leads to defective tumor clearance in vivo.
Figure 14B:
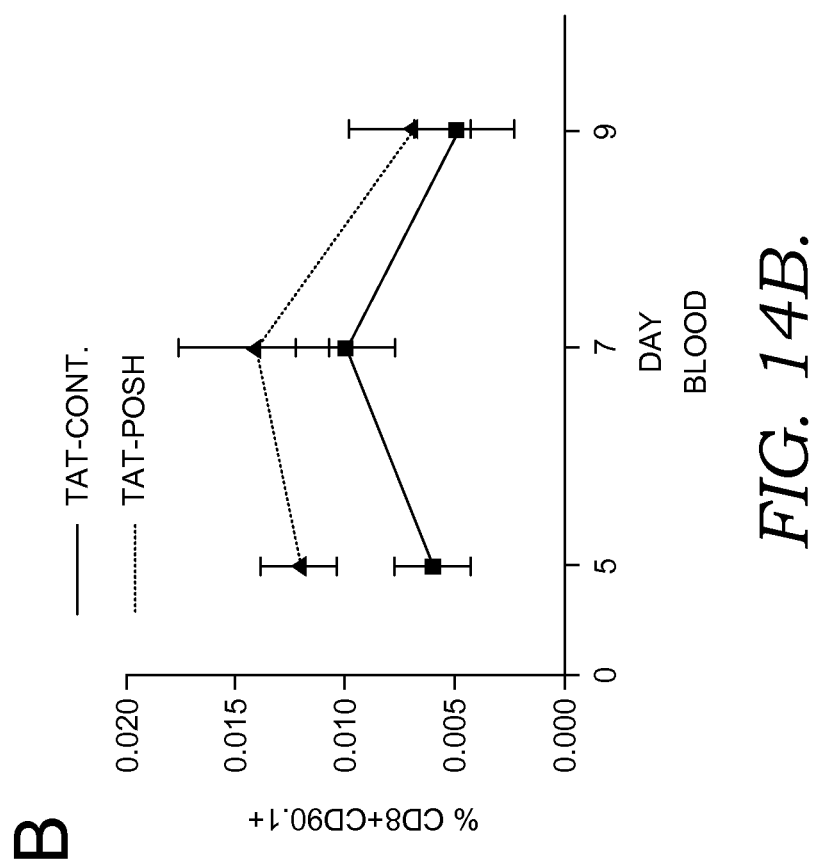
Figure 14C:
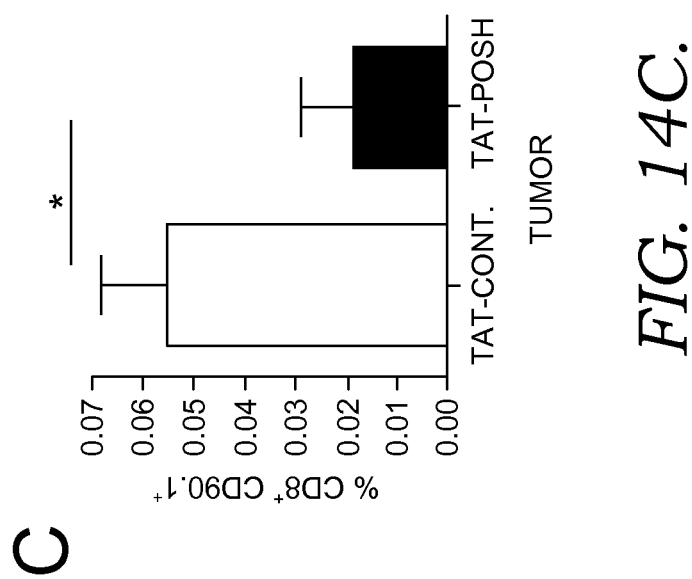
Figure 14D:
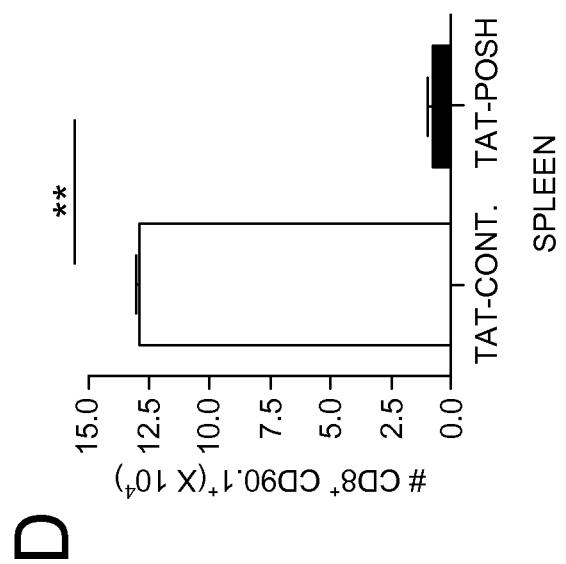

To test the effect of disruption of the POSH/JIP-1 scaffold complex on CD8+ T-cell effector function in a more physiological setting, we investigated the ability of Tat-POSH treated CTL to control tumors in vivo. CD8+ OT-I T cells were stimulated for 2 days in vitro in the presence of Tat-POSH or control peptide. To directly test effector function and partially correct for the proliferation defect, equal numbers (1×10$^6$) of Tat-POSH and Tat-cont. CD90.1+ CTLs were transferred into B6 Rag−/− CD90.2 congenic hosts that had been subjected to sub-cutaneous inoculation with large doses (5×10$^5$ cells) of the OVAp expressing thymoma (EG7). Tumor size was tracked for 20 days and compared to a cohort of B6 Rag−/− hosts that received the tumor with no CTL. The Tat-control treated CTL group had significantly smaller tumors than the Tat-POSH treated CTL and the no CTL control groups. Furthermore, there was no difference in tumor size between Tat-POSH treated and no CTL control group (FIG. 14A). These results are consistent with loss of INF-γ dependent tumor control by JNK1−/−, Eomes−/− and Eomes−/−/T-Bet−/− CD8 T cells. Interestingly, there was no difference in cell number or percentage of CTL in the blood of mice from either group over the first 9 days (FIG. 14B). However, when tumor specific T-cell numbers were analyzed at day 20, there was a sizeable (>10 fold) reduction in both the number of Tat-POSH treated CTL in the spleen (FIG. 14C) and tumor-infiltrating lymphocytes (TIL) in the Tat-POSH treated group (FIG. 14D). Curiously, in spite of this marked loss of Tat-POSH treated CTL late in the response, we did not observe significant differences in apoptosis between Tat-POSH and control treated cells in the blood, spleen or tumor (data not shown). Regardless, the loss of tumor specific CTL along with their reduced effector function (TNF-α, FasL and IFN-γ; FIG. 13) provide convincing evidence that the POSH/JIP-1 complex regulates JNK1-dependent development of effector function important for tumor clearance by CD8+ T cells.

Experimentally, to show that the disruption of POSH/JIP-1 network leads to defective tumor clearance in vivo, CD90.1+ OT-I T cells were stimulated with OVAp-pulsed APCs in the presence of Tat-cont. or Tat-POSH for 48 hours. 1×10$^6$ of the activated CD90.1+ OT-I T cells were then transferred into B6 Rag−/− host that were inoculated 2 days earlier with 5×10$^5$ EG7 cells SC. (A) Tumor size (mm) was monitored every other day for 24 days. In FIG. 14, graph depicts mean±SEM. Frequency of CD90.1+ OT-I T cells was determined in blood (FIG. 14B) at the times shown, the tumor (FIG. 14C) and spleen (FIG. 14D) at day 24. Data are shown as mean±SD and are from 2 independent experiments with cohorts of n=15 and n=25. * p≤0.05, ** p≤0.01; 2-tailed Student t test, 2-way Anova, Log-rank (Mantel-Cox).

Disruption of POSH/JIP-1 Transiently Inhibits T-Bet and Blocks Eomes Activation.

Figure 15A:
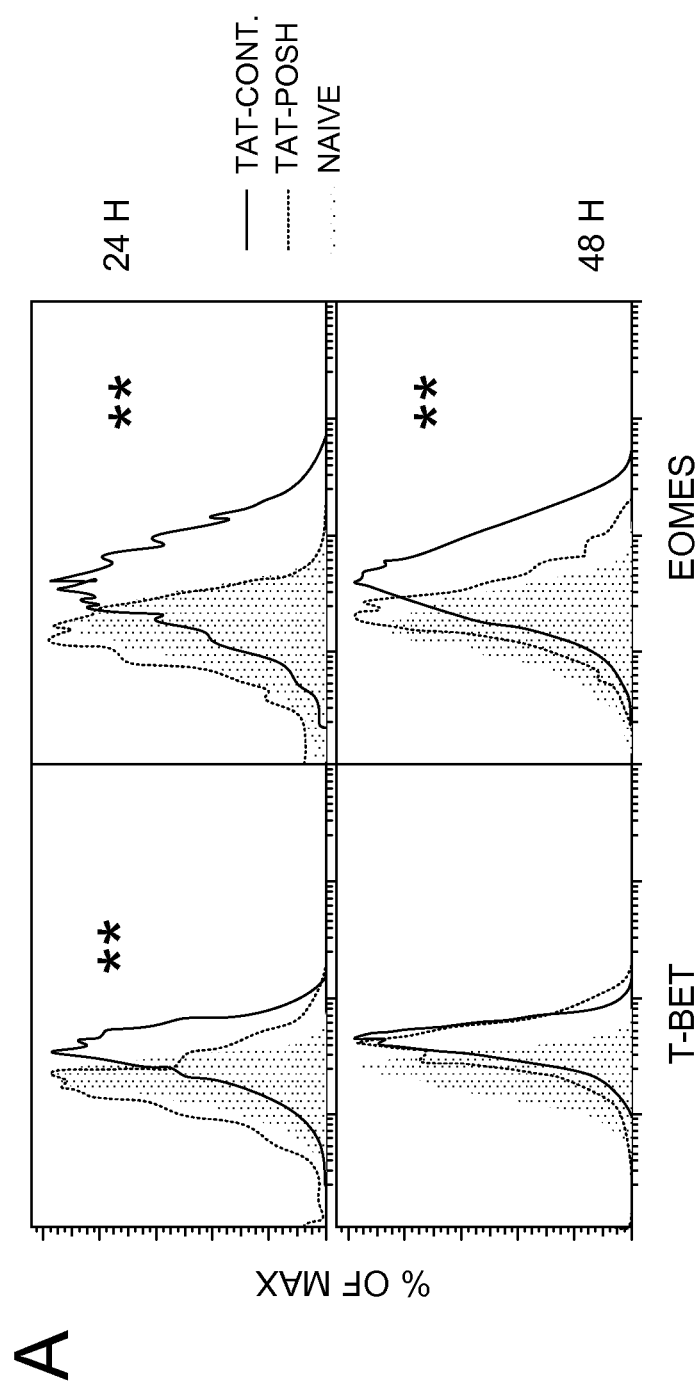
FIGS. 15(A) to 15(D) illustrate how the POSH/JIP-1 scaffold network regulates T-bet and Eomes expression in CD8$^+$ T cells.
Figure 15B:
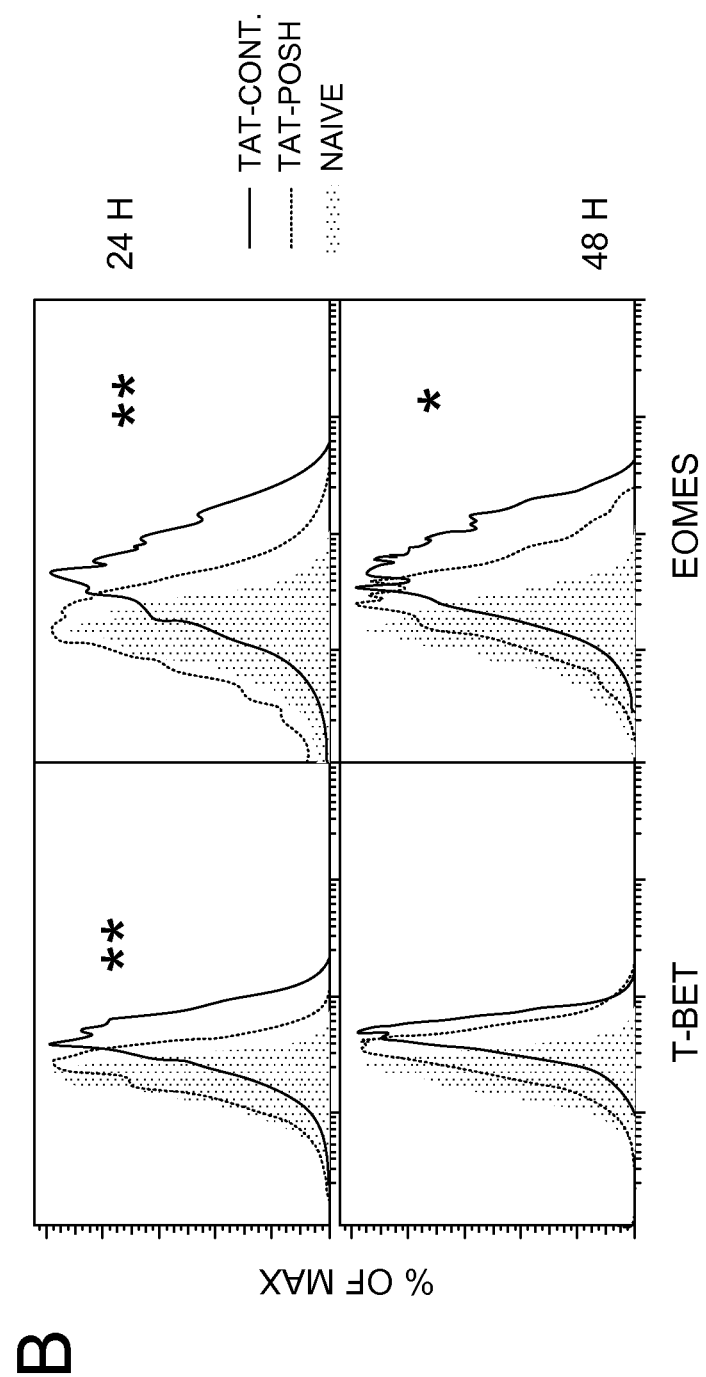
Figure 15C:
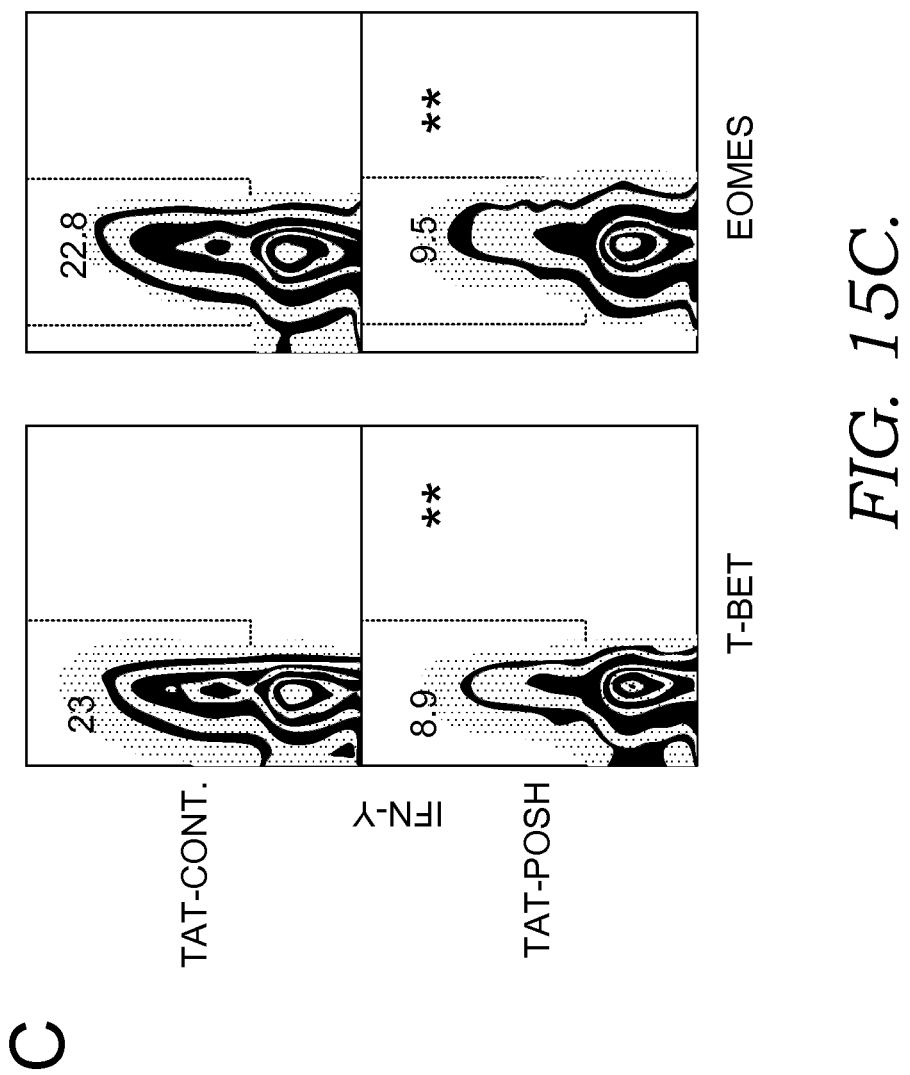
Figure 15D:
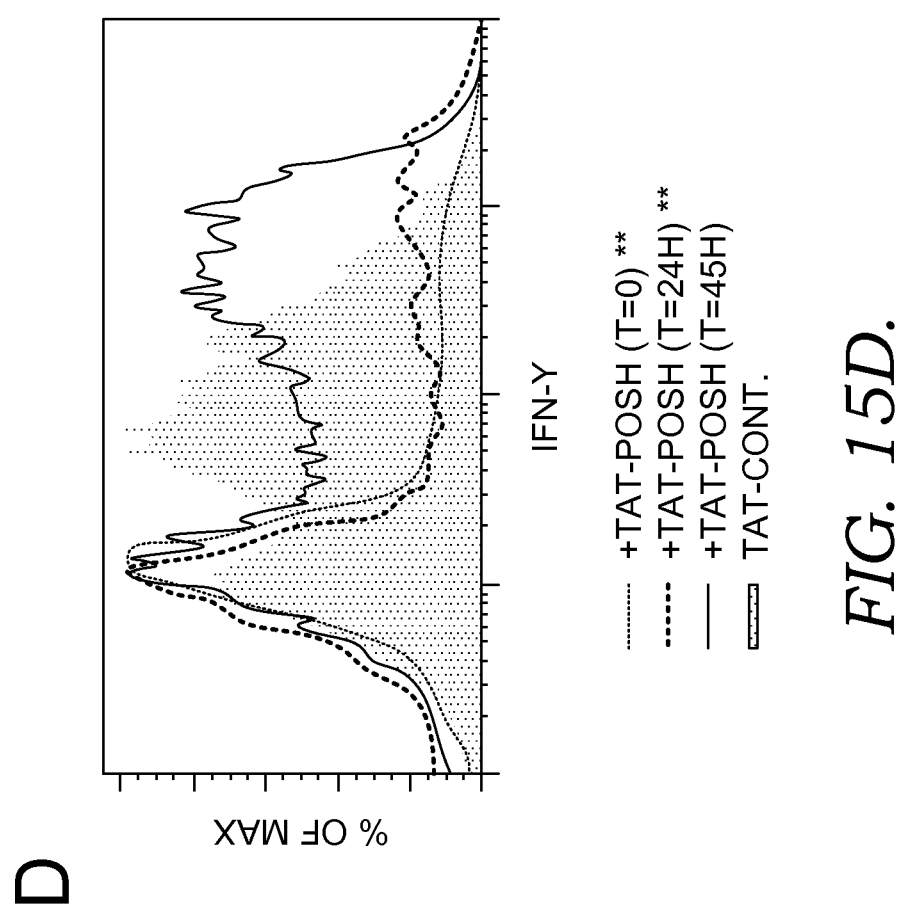

Intriguingly, Tat-POSH treated CTL did not recover their defect even when they had been washed, adoptively transferred and exposed to their cognate antigen (FIG. 14). This suggests that the POSH/JIP-1 complex regulates the programming of CD8+ T-cell differentiation and effector function. Thus, since JNK1, through T-bet and Eomes have a role in programing CTL effector function and tumor clearance, we tested the expression of these transcription factors at 24 and 48 hours in OT-I T cells stimulated with peptide-pulsed APCs in the presence of Tat-POSH, Tat-control peptide or the pan kinase inhibitor of JNK, SP600125. In the presence of Tat-POSH, T-bet expression was markedly reduced at 24 hours but was recovered by 48 hours (FIG. 15A). These were comparable with the levels of T-bet induced in the presence of SP600125 (FIG. 15B). This suggests that the POSH/JIP-1 complex has a role in the early induction of T-bet expression but may not at later time points. On the other hand, Eomes was significantly impaired at 24 and 48 hours in the presence of Tat-POSH (FIG. 15A). Neither the Tat-POSH nor the control treated CTL (day 4) up-regulated T-bet or Eomes despite the ability of the control group to produce INF-γ (FIG. 15C). The results up to this point suggest the major role for POSH/JIP-1 complex is early in the response. To test this, naïve OT-1 T cells were stimulated and kept in constant presence of Tat-POSH (t=0), or Tat-POSH was added 24 h or 48 h after stimulation. The cells were then kept in presence of the inhibitor until day 4 when we tested their ability to express IFN-γ upon restimulation. CTL that were in the continuous presence of Tat-POSH (t=0) or inhibited 24 hrs post stimulation (t=24) had significant deficiencies in INF-γ expression (FIG. 13, 15D). Strikingly, cells treated with Tat-POSH at 48 hrs post stimulation expressed INF-γ at levels comparable to control treated cells (FIG. 15D). These data indicate that POSH/JIP-1 interaction is important for programing effector function early (first 48 hours). Furthermore, the JNK1 dependent defect in early T bet and Eomes expression may describe the mechanism for defective IFN-γ expression observed here.

Figure 16A:
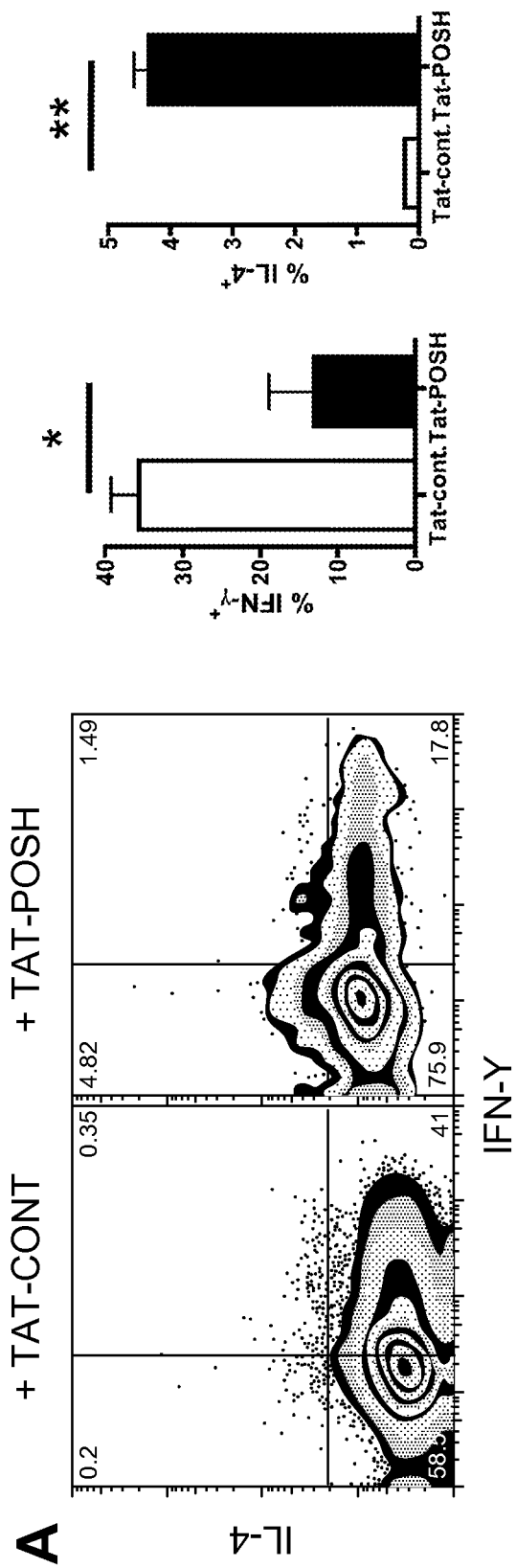
FIGS. 16(A) to 16(B) demonstrate how POSH regulates T$_H$1/T$_H$2 polarization via induction of T-bet.
Figure 16B:
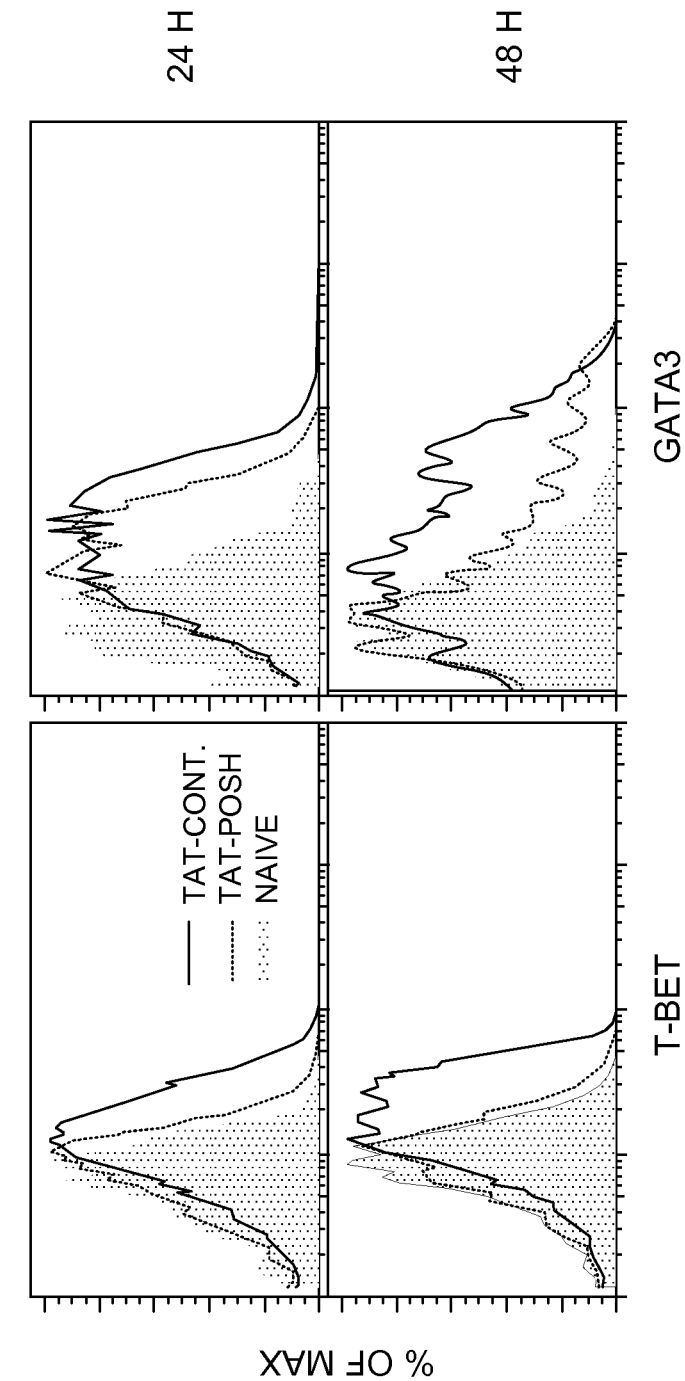

To show that POSH/JIP-1 scaffold network regulates T-bet and Eomes expression in CD8⁺ T cells, naïve OT-I T cells were stimulated with OVAp-pulsed APCs in the presence (A) Tat-cont. or Tat-POSH peptide; (B) the JNK inhibitor SP600125 or vehicle control for 24 and 48 hours and the levels of T-bet and Eomes were determined by IC. In FIG. 15C, OT-1 CTL were re-stimulated as in FIG. 4 on day 4 with BFA and stained for Eomes or T-bet and IFN-γ. FIG. 15D shows naïve T cells stimulated as in FIG. 15A and Tat-POSH was present throughout (t=0), 24 hours post stimulation (t=24) or 48 hours post stimulation (t=48). Cells were re-stimulated on day 4 and IFN-γ was measured as in FIG. 13. All data in FIG. 15A-D are representative of 3 independent experiments. * p≤0.05;** p≤0.01; 2-tailed Student t test. In addition, FIG. 16 shows that POSH regulates $T_H1/T_H2$ polarization via induction of T-bet.

Figure 17:
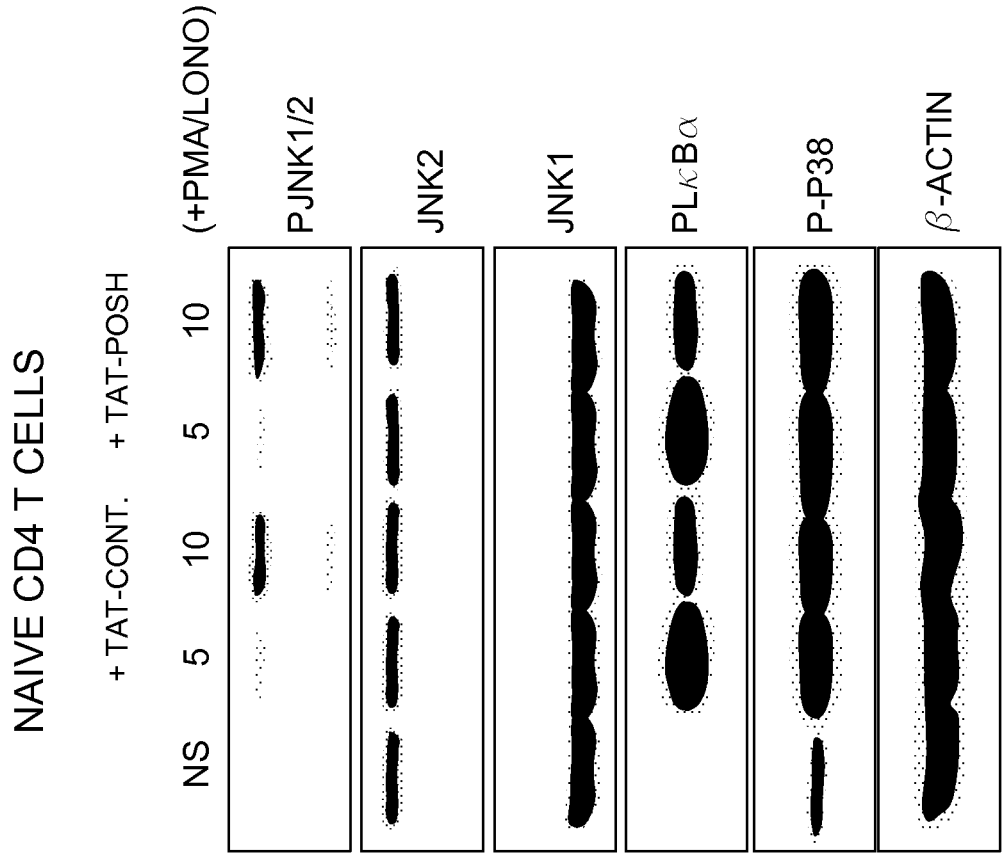
FIG. 17 demonstrates that disruption of POSH function in naïve CD4 T cells has little or no effect on JNK (or NFkB) activation.

POSH has a unique role depending on the developmental state of the CD4 T cell. Unlike CD8 T cells, disruption of POSH function in naïve CD4 T cells has little or no effect on JNK (or NFkB) activation (FIG. 17).

Nothing is known about the function of POSH in B cells. JNK deficiency has no effect on B cell development but may have a role in peripheral homeostasis. JNK signals through CD40 to activate JNK, c-JUN and cyclin D2 for germinal center formation and antibody production, important B cell effector functions. Interestingly, transformation of pre-B cells by BCR-ABL in vivo and in vitro is impaired in JNK1-deficient mice. This defect could be rescued by expression of Bcl2, indicating that JNK1 can provide survival signals for BCR-ABL-transformed B-ALL (Accute Lymphoblastic Leukemia). It is known that inactivation of JNK in *Theileria*-transformed B lymphocytes also leads to lymphocyte apoptosis. Therefore, while JNK may mediate cell death or inhibit proliferation in normal B cells, it provides survival signals in leukemic B cells. Constitutive BCR signaling has been connected to basal growth of B lymphoma. The BCR connects to JNK1 through Ezrin or Rac1 and PLcγ2. Therefore we hypothesized if POSH has a role in JNK1 regulation in B cells; we would expect to see a response to Tat-POSH treatment in B cell leukemia.

Figure 18A:
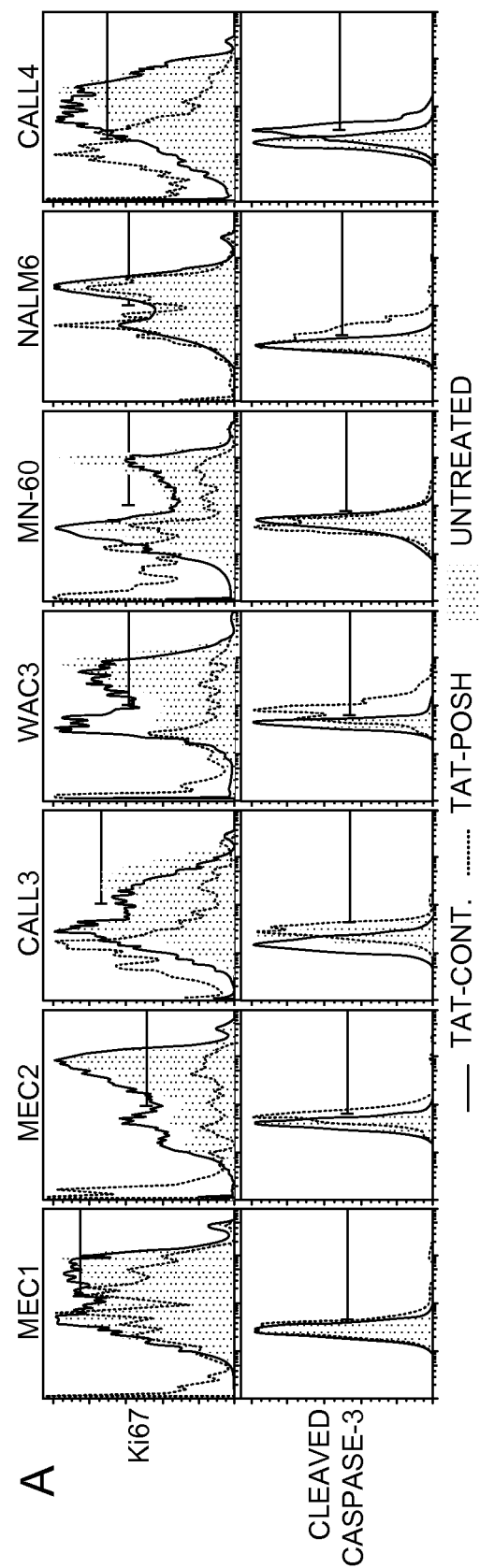
FIGS. 18(A) to 18(C) demonstrate the dramatic effect of Tat-POSH treatment on multiple B cell leukemias.
Figure 18B:
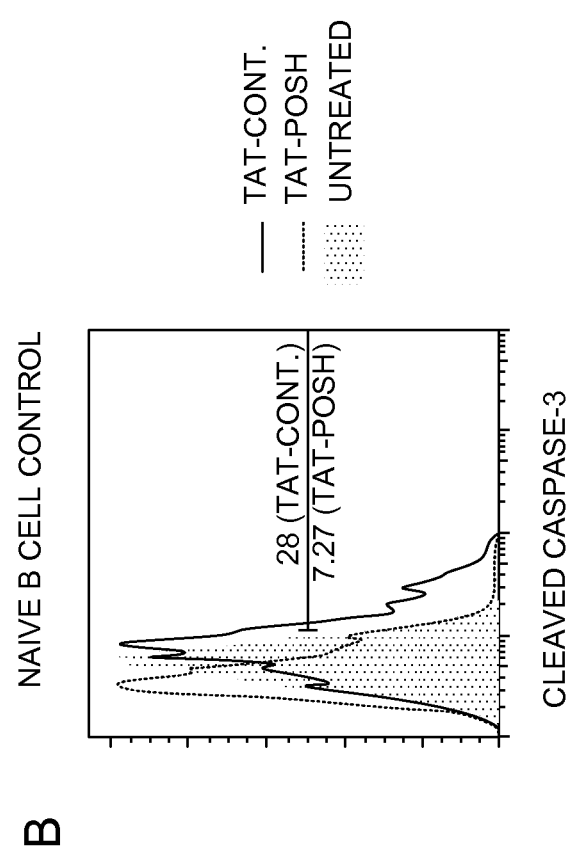
Figure 18C:
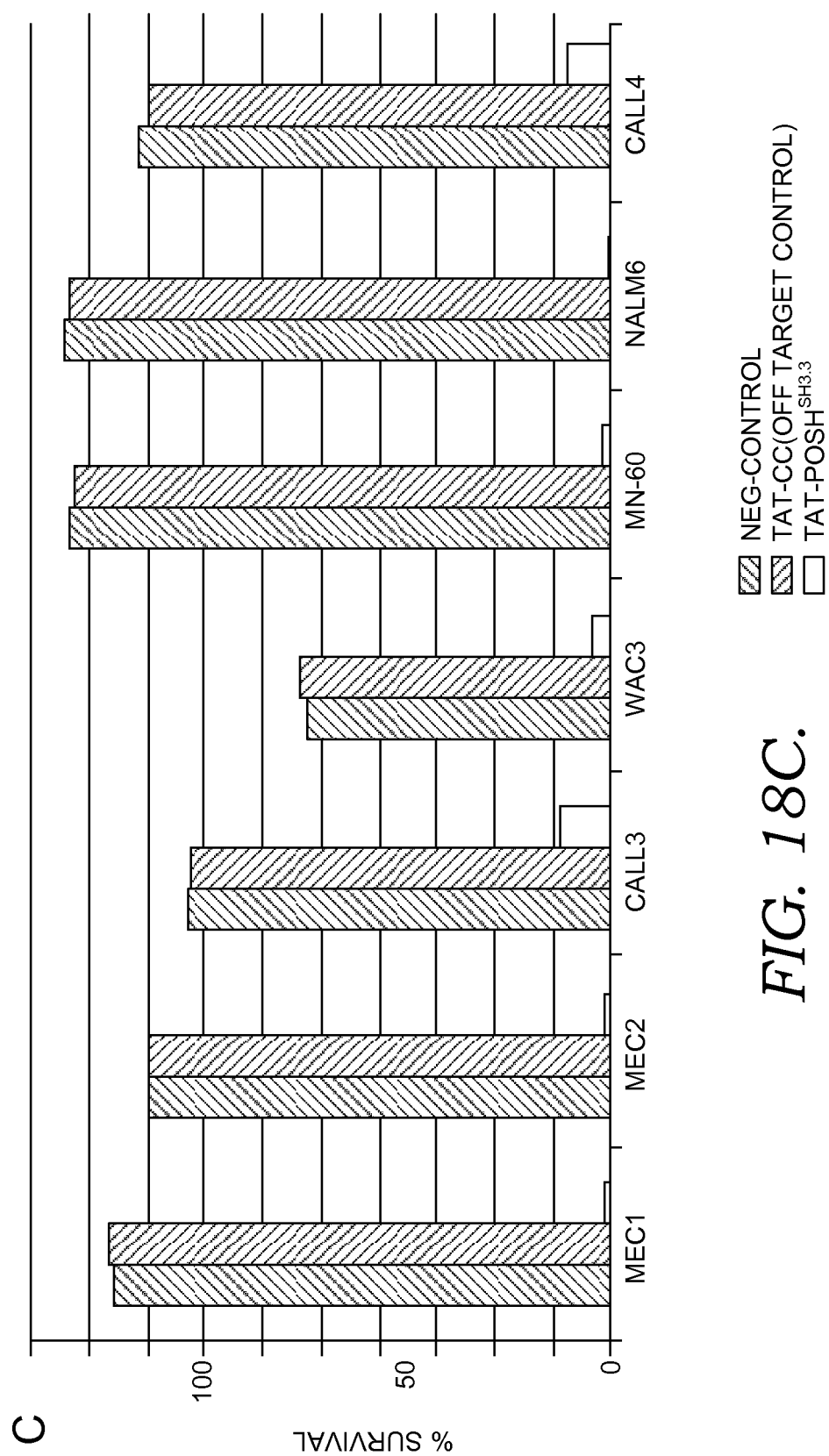

To test this we cultured 3 human B-CLL (Chronic Lymphoblastic Leukemia) and human 4 B-ALL cell lines in the presence of Tat-POSH or Tat-control. These cells have a diverse set of genetic abnormalities that contribute to their oncogenesis. Mec1 and Mec2 are serial samples of prolymphocytic B-CLL. They over express Bcl2, Bax, BclxL and low BclxS. MHH-Call3 is a PCB-ALL that have a TCF3 (E2A)/PBX1 translocation. Wac3 is an EBV transformed B cell. MN-60 is a B-ALL (Burkitt's lymphoma) with a IgH/MYC translocation.Nalm6 is a PCB-ALL. MHH-Call4 is a PCB-ALL with an IgH/CRLF2 translocation. At days 2 and 4 we measured cell cycle progression with Ki-67, apoptosis with cleaved caspase 3 and measured survival by forward scatter/side scatter (FSC/SSC), all by flow cytometry. Remarkably, each cell line was sensitive to treatment (FIG. 18). So much in fact that at 48 hours there were nearly no cells left alive in the Tat-POSH treated samples. There is a marked reduction in Ki-67 for all of the cell lines except for B-CLL, Mec-1 and the B-ALL Nalm6 (FIG. 18A). For cleaved caspase 3, each cell line had a subtle yet significant increase in expression (FIG. 18A). Interestingly, Tat-POSH had the opposite effect on normal primary mouse B cells in culture (FIG. 18B). The most dramatic data for this experiment is the highly significant loss of survival in the presence of Tat-POSH (FIG. 18C). Excitingly, we get to be the first to say, that POSH is a critically important component of the survival program of various forms of B cell leukemia.

Figure 19A:
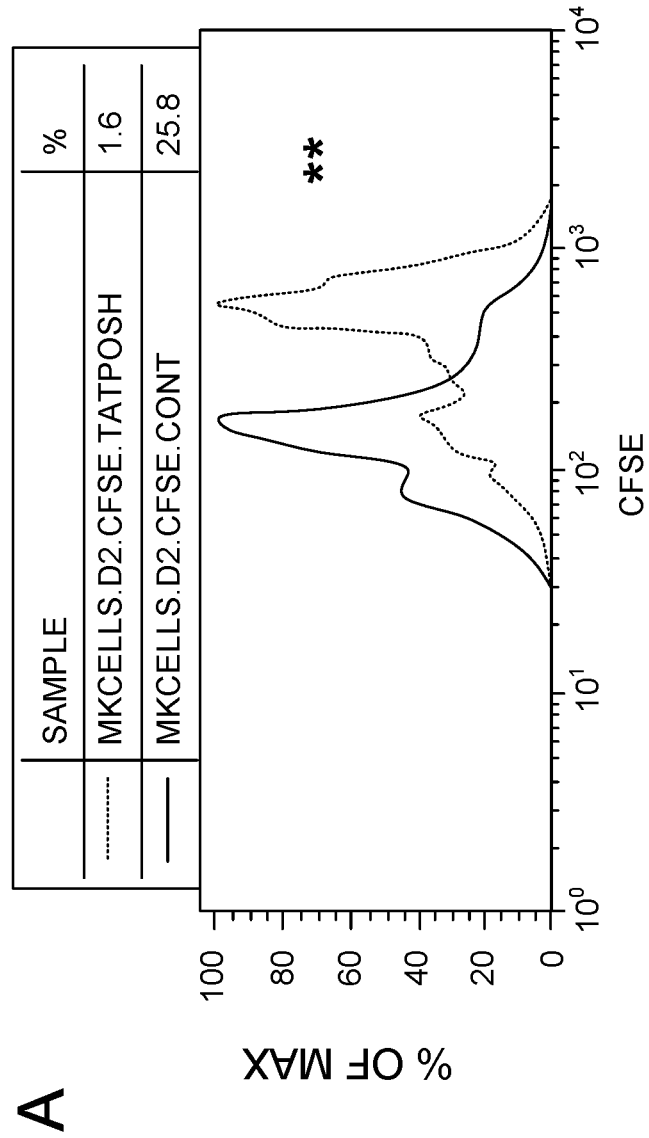
FIGS. 19(A) to 19(C) demonstrate how Tat-POSH blocks proliferation and kills leukemia cell lines.
Figure 19B:
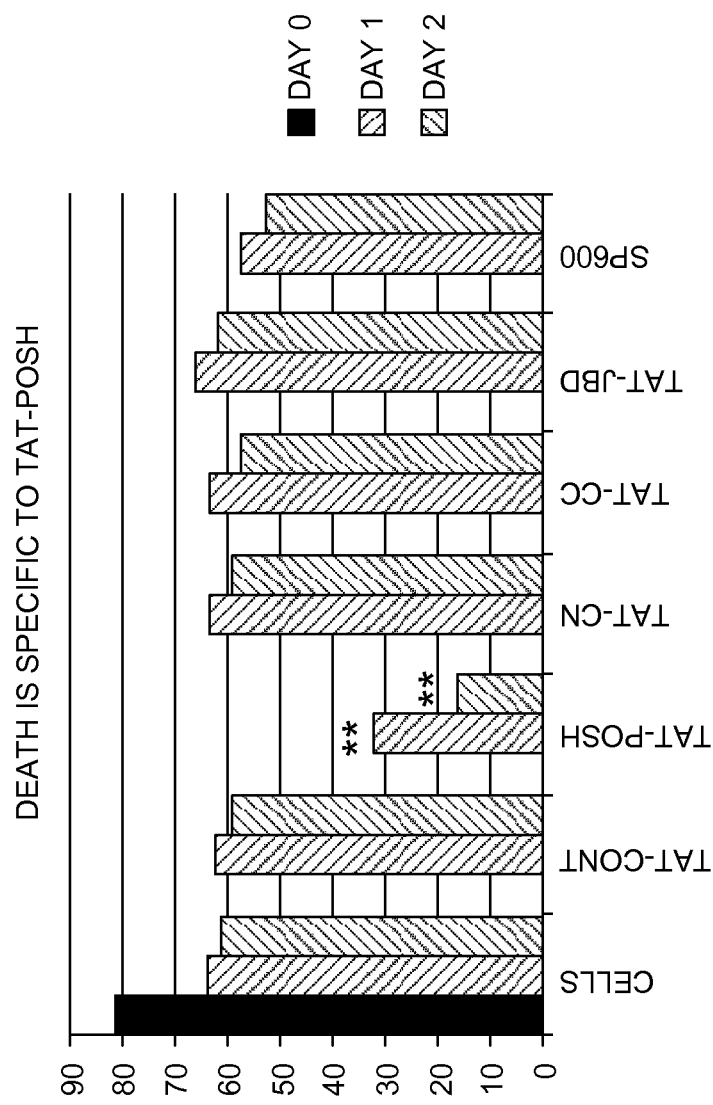
Figure 19C:
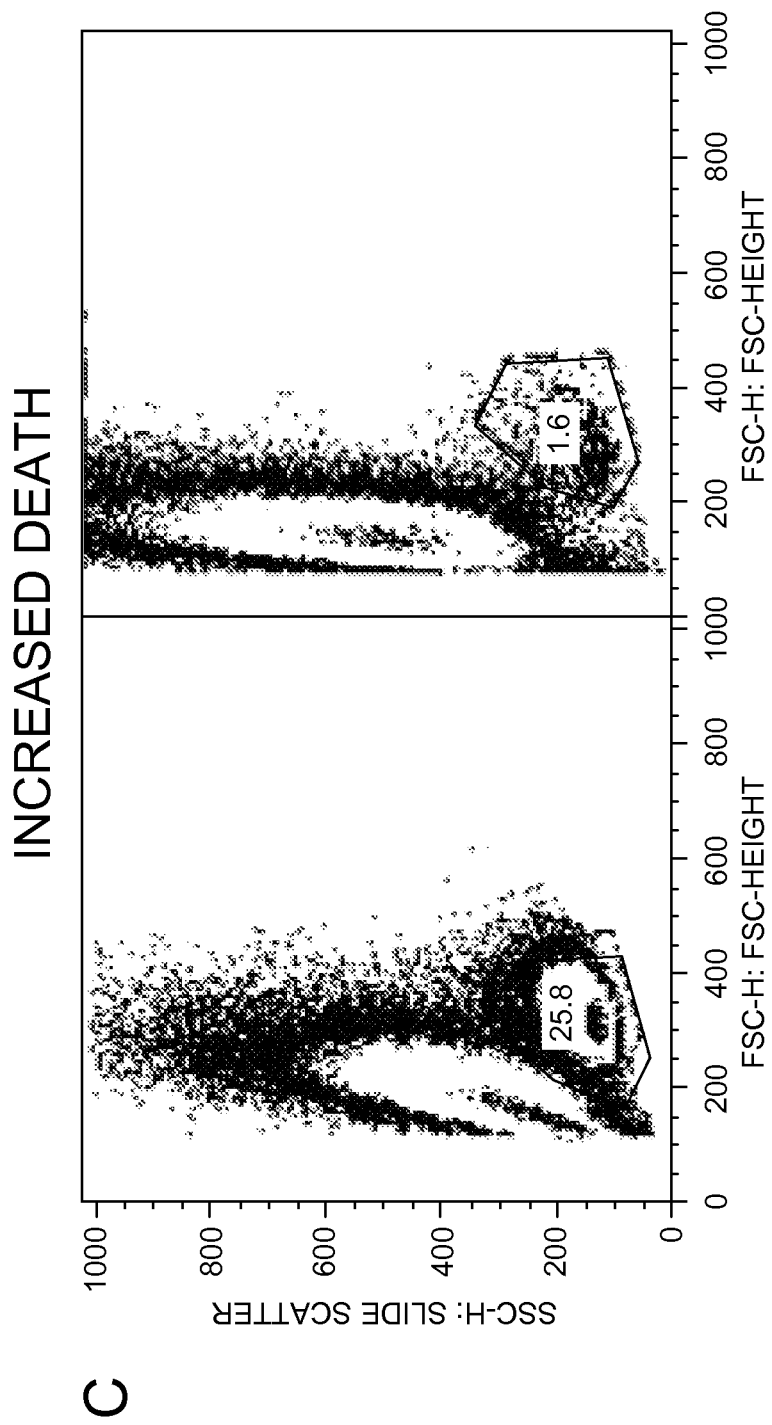

To test if Tat-POSH specifically blocks proliferation and kills leukemia cell lines, the T cell leukemia line Mkat was incubated with 3e-6 M Tat-POSH or control peptides for 48 hours and cell division, survival and markers of apoptosis are measured as shown in FIG. 19A-C. Commercially available JNK inhibitors and negative control peptides had no effect on the survival of tested cells, while in the presence of Tat-POSH, highly significant loss of survival was found (FIG. 19).

Figure 20:
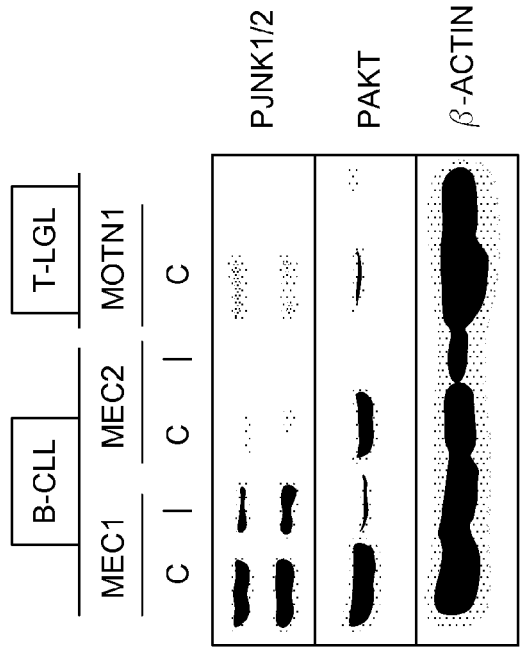
FIGS. 20(A) to 20(B) demonstrate how Tat-POSH disrupts survival through inhibition of JNK and or AKT activation in chronic B cell leukemia (B-CLL) and T cell large granular lymphoma.
Figure 20:
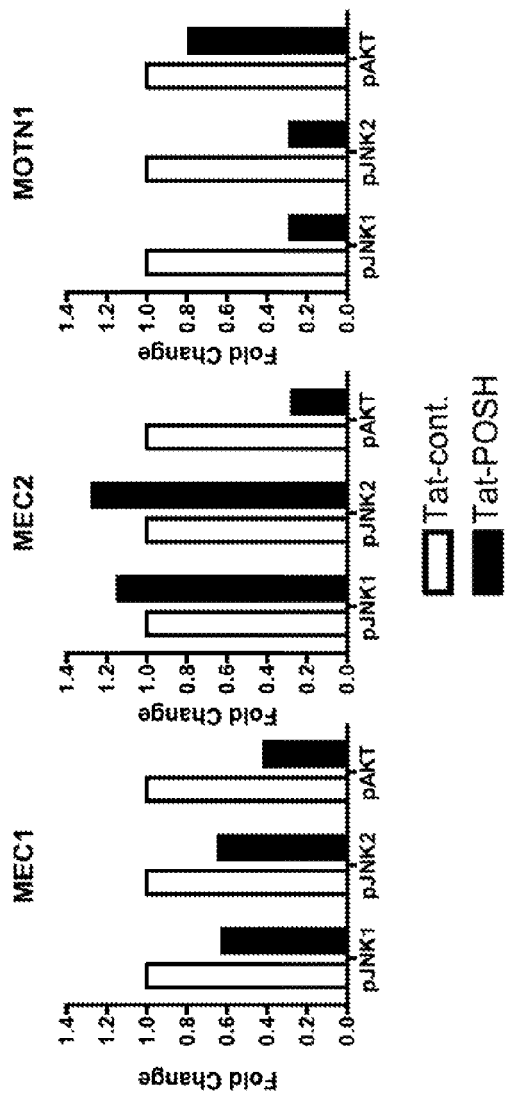

FIG. 20 shows that Tat-POSH disrupts survival through inhibition of JNK and or AKT activation in chronic B cell leukemia (B-CLL) and T cell large granular lymphoma. Cells were incubated for 24 hours with Tat-Cont or Tat-POSH followed by lysis and immunoblot analysis for active JNK and AKT. FIG. 20B represents densitometetry of immunoblot shown. In FIG. 20, data are representative of n=3.

We have also performed tests on a triple negative breast cancer (TNBC) cell line and a lung cancer cell line known to be dependent on JNK1. In both cases cells were treated as indicated above, with the addition of Tat-POSH SH3.4 (SEQ ID NO: 13). In the case of the TNBC we saw a modest but significant reduction in proliferation (10-15%) but a marked increase in death in Tat-POSH treated cells (data not shown). Interestingly, the cells also exhibited a remarkable change in their morphology (they rounded up) suggesting the potential loss of migratory capabilities that would reduce their metastatic potential. This was demonstrated in the presence of Tat-POSH SH3.3 (SEQ ID NO: 12) and Tat-POSH SH3.3 &SH3.4 (SEQ ID NO: 12 and SEQ ID NO: 13, respectively). The lung cancer cell line showed a remarkable increase in apoptosis in the presence of Tat-POSH indicating these inhibitors may have a broad range of uses for multiple types of cancer including but not limited to leukemia, breast cancer, lung cancer, hepatocarcinoma and prostate cancers (the latter two have well defined dependence on signals potentially upstream and downstream of JNK).

Figure 21:
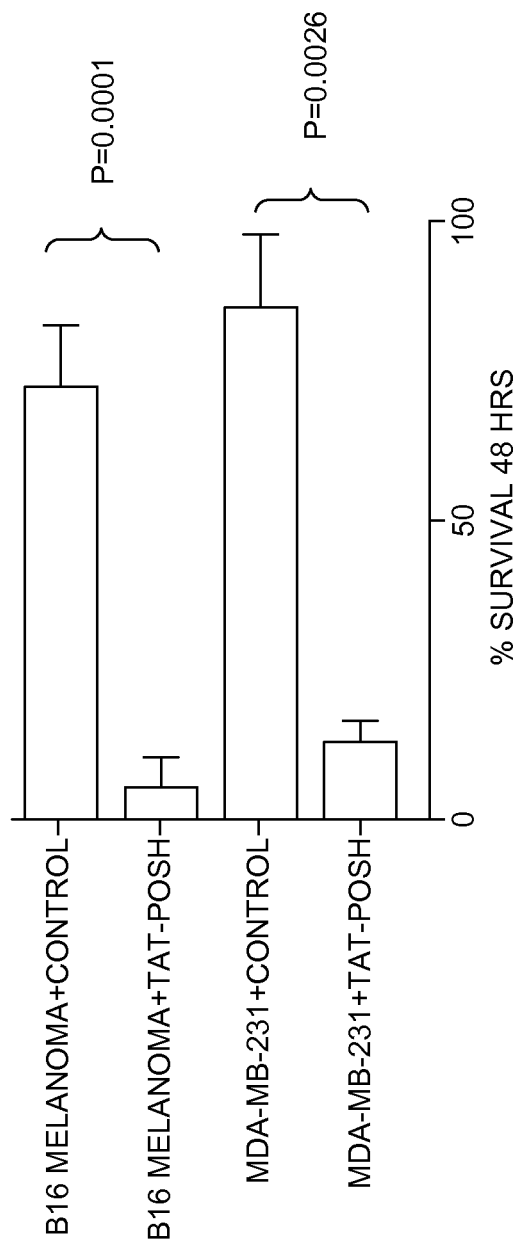
FIG. 21 demonstrates that melanoma and breast cancer lines are also susceptible to treatment with TAT-POSH.
Figure 22:
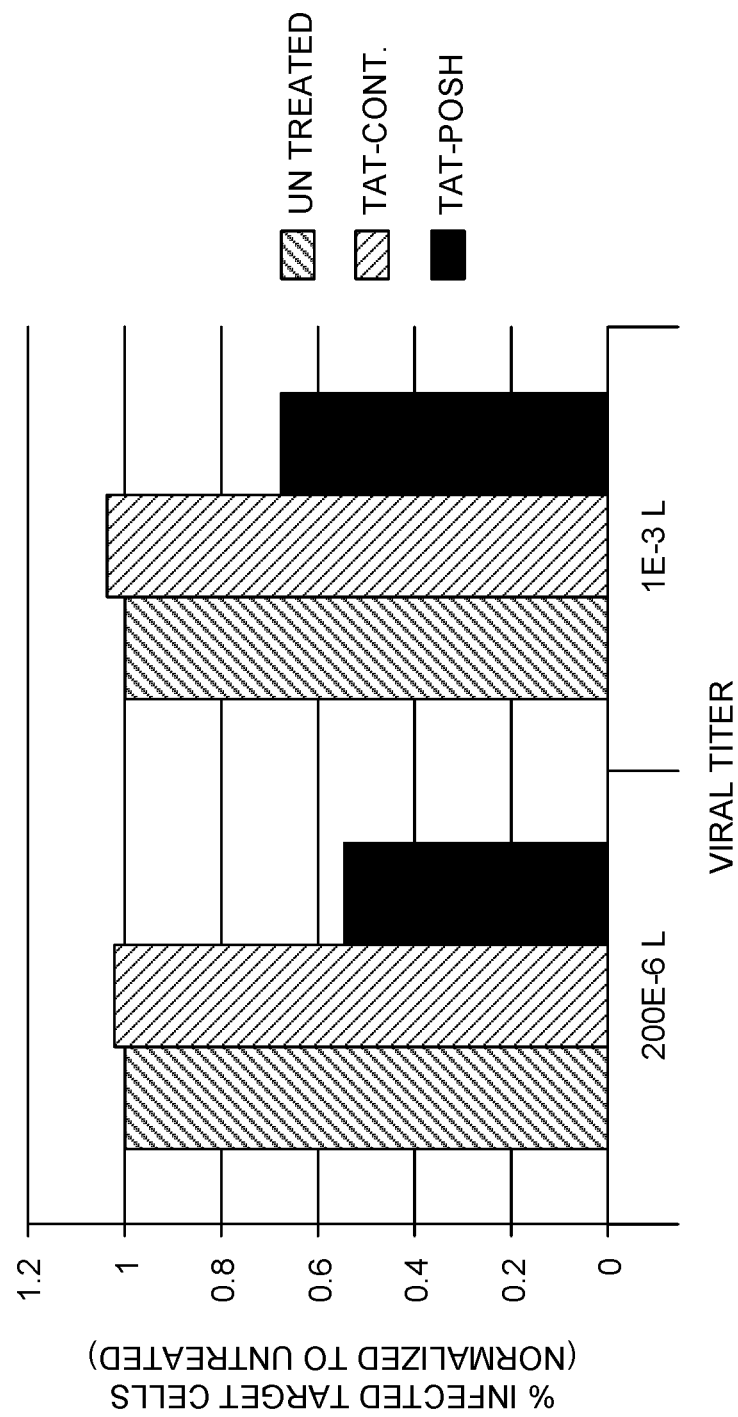
FIG. 22 demonstrates Tat-POSH SH3.3 modest reduction in viral release in HIV infected cells.

FIG. 21 shows that Melanoma and Breast cancer lines are also susceptible to treatment with TAT-POSH. The mouse melanoma cell line treated with Tat-control or Tat-POSH$^{SH3.3}$ (SEQ ID NO: 12) or the triple negative human breast cancer was treated with control or Tat-POSH$^{SH3.3}$ (SEQ ID NO: 12)+Tat-POSH$^{SH3.4}$ (SEQ ID NO: 13) for 48 hours in vitro. Death was assessed by flow cytometry. Graphs of FIG. 21 show mean+/−SD. Data representative of n<3. p values calculated Tat-POSH SH3.3 (SEQ ID NO: 12) induces a modest reduction in viral release in HIV infected cells as is shown in FIG. 22. Cells infected with HIV were untreated or incubated with the negative control Tat-cont. or Tat POSH SH3.3 (SEQ ID NO: 12). Data measures the infectivity (viral titer) and correlates with inhibition of Alix dependent release of HIV viral particles. FIG. 22 shows that Tat-POSH SH3.3 (SEQ ID NO: 12) induces a modest reduction in viral release in HIV infected cells.

Future directions and additional tests for Tat-POSH SH3.3 (SEQ ID NO: 12) to investigate their effect on apoptosis in triple negative breast cancer cells (SH3.3 and SH3.3+ SH3.4), apoptosis in TPL-2 dependent lung cancer, and if those compounds can block cell division in leukemia cell line (EL-4) but does not induce increased apoptosis during first 48 hours.

---

What is claimed is:

1. A composition comprising at least one chimeric peptide, wherein the at least one chimeric peptide comprises: i) a first amino acid portion comprising the amino acid sequence selected from the group consisting of: EGKEPGDLKFSKGDIIILRR (SEQ ID NO: 1); KEADKDCLPFAKDDVLTVIR (SEQ ID NO: 2); RKEDELELRKGEMFLVFER (SEQ ID NO: 3); PQSEAELELKEGDIVFVHKK (SEQ ID NO: 4); and an amino acid sequence having over its total length at least 85% sequence identity with any one of SEQ ID NOs: 1 to 4; and ii) a second amino acid portion comprising a cell internalization moiety adapted to internalize the at least one chimeric peptide into a cell to bind to POSH (Plenty of SH3 Domains) for inhibiting and disrupting POSH scaffold networks.

2. The composition of claim 1, wherein the first amino acid portion comprises an amino acid sequence having over at least 90% overall sequence identity with any one of SEQ ID NOs: 1 to 4.

3. The composition of claim 1, wherein the first amino acid portion is of mammalian origin.

4. The composition of claim 1, wherein the first amino acid portion is encoded by a nucleic acid sequence.

5. The composition of claim 1 in which the cell internalization moiety comprises a peptide of HIV tat.

6. The composition of claim 5, in which the cell internalization moiety comprises the amino acid sequence of GRKKRRQRRR (SEQ ID NO: 5).

7. The composition of claim 1, wherein the composition is a pharmaceutical composition together with one or more pharmaceutically acceptable carrier and/or excipients.

8. A chimeric peptide comprising a peptide sequence for inhibiting and disrupting POSH scaffold networks and a protein transduction domain, wherein the peptide sequence comprises the amino acid sequence selected from the group consisting of: EGKEYGDLKESKGDIIILRR (SEQ ID NO: 1); KEADKDCLPFAKDDVLTVIR (SEQ ID NO: 2); RKEDELELRKGEMFLVFER (SEQ ID NO: 3); PQSEAELELKEGDIVFVHKK (SEQ ID NO: 4); and an amino acid sequence having over its total length at least 85% sequence identity with any one of SEQ ID NOs: 1 to 4.

9. The chimeric peptide of claim 8, wherein the protein transduction domain comprises a peptide of HIV tat comprising the amino acid sequence of GRKKRRQRRR (SEQ ID NO: 5).

10. A pharmaceutical composition comprising at least one peptide of claim 8 as active ingredient, together with one or more pharmaceutically acceptable carrier and/or excipients.

* * * * *